United States Patent [19]

Peel, III

[11] Patent Number: 5,895,359
[45] Date of Patent: Apr. 20, 1999

[54] SYSTEM AND METHOD FOR CORRECTING A LIVING SUBJECT'S MEASURED BLOOD PRESSURE

[75] Inventor: Harry H. Peel, III, San Antonio, Tex.

[73] Assignee: Southwest Research Institute, San Antonio, Tex.

[21] Appl. No.: 08/870,456

[22] Filed: Jun. 6, 1997

[51] Int. Cl.$^6$ ............................................. A61B 5/00
[52] U.S. Cl. ............................................... 600/494
[58] Field of Search .............................. 600/490, 491, 600/492, 493, 494, 495, 496, 500

[56] References Cited

U.S. PATENT DOCUMENTS 5,131,391  7/1992  Sakai et al. .
5,752,920  5/1998  Ogura et al. ........................... 600/494

FOREIGN PATENT DOCUMENTS 0 123 313   10/1984  European Pat. Off. .
0 815 790 A1   1/1998  European Pat. Off. .
0 821 910 A2   2/1998  European Pat. Off. .

*Primary Examiner*—Scott M. Getzow
*Attorney, Agent, or Firm*—Oliff & Berridge, PLC

[57] ABSTRACT

A system and method for correcting a living subject's measured blood pressure when the living subject's actual blood pressure changes during an oscillometric blood pressure measurement detects oscillometric pressure pulse waves produced by a cardiac muscle of the living subject, measures a blood pressure of the living subject based on the amplitudes of the oscillometric pressure pulse waves, and corrects the measured blood pressure when the living subject's blood pressure changes during the blood pressure measurement. The system and method of this invention preferably determine an estimated blood pressure of the living subject, monitor the estimated blood pressure, and determine that the living subject's blood pressure changed during the blood pressure measurement when the estimated blood pressure changes by a predetermined amount during the blood pressure measurement. When the living subject's blood pressure is determined to have changed during the blood pressure measurement, the system and method of this invention display an estimated systolic blood pressure for the time at which the living subject's diastolic blood pressure was measured.

20 Claims, 23 Drawing Sheets

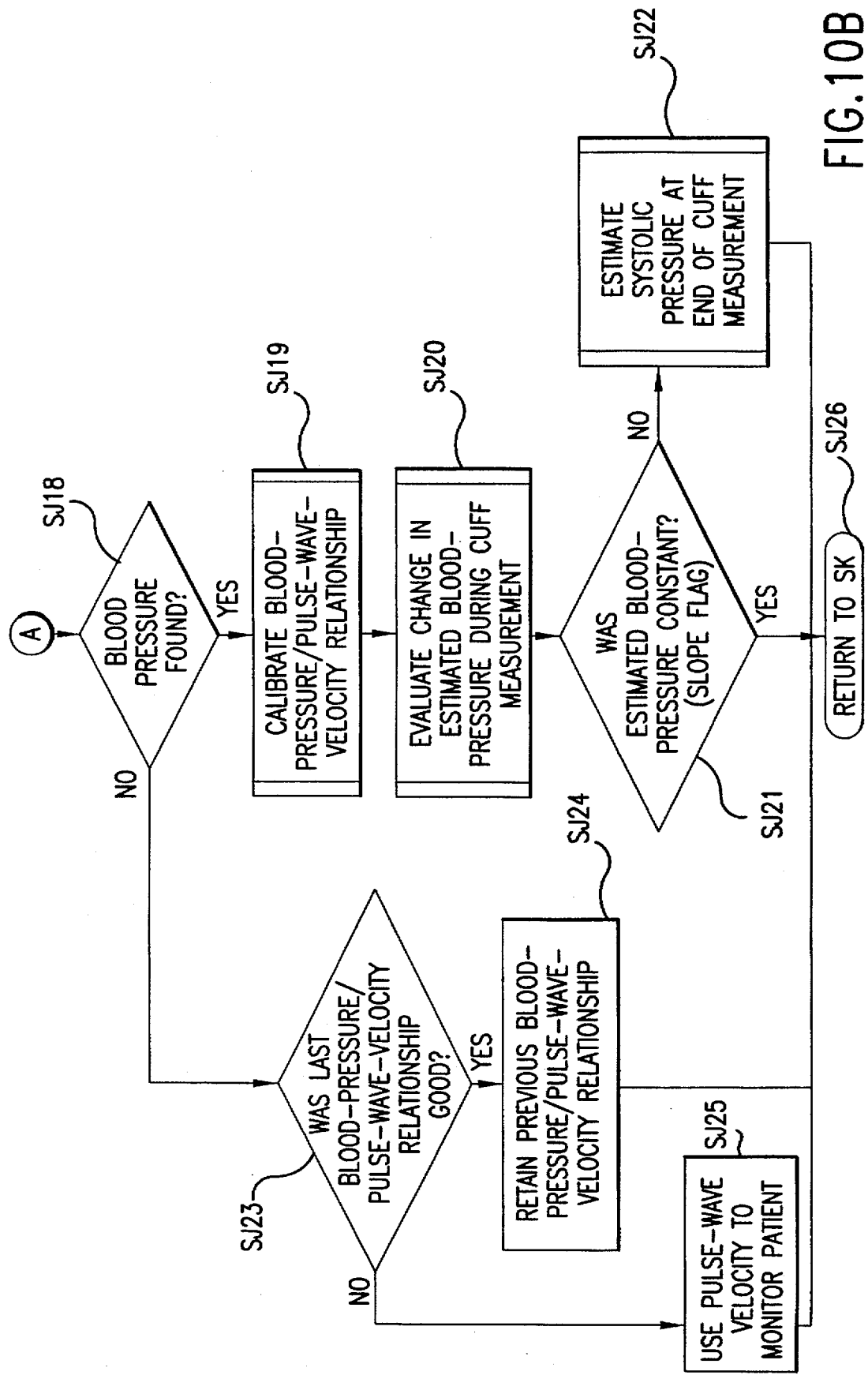

SYSTEM AND METHOD FOR CORRECTING A LIVING SUBJECT'S MEASURED BLOOD PRESSURE

BACKGROUND OF THE INVENTION

1. Field of Invention

This invention relates to medical diagnostic and monitoring systems. More specifically, this invention is directed to a system and method for accurately monitoring the cardiovascular state and physiologic condition of a living subject.

2. Description of Related Art

Blood-pressure measurement devices are commonly used to diagnose certain ailments, such as arteriosclerosis, and to monitor a living subject's cardiovascular or physiologic state.

A blood-pressure measurement device typically measures the living subject's blood pressure indirectly with the use of a cuff that is wrapped around a portion of the living subject. The cuff applies pressure to the living subject. The living subject's blood pressure is then measured using a well-known oscillometric method, which is based on detecting changes in the amplitude of a heartbeat-synchronous pulse wave as the pressure applied by the cuff is gradually decreased.

The accuracy of this indirect blood-pressure measurement method is dependent upon a number of design factors, such as the size of the cuff relative to the circumference of the appendage that the cuff is wrapped around, the accuracy of the pressure-sensing devices used by the blood-pressure measurement device, and the performance of the algorithm used to calculate the living subject's systolic, diastolic and mean blood pressures.

An indirect blood-pressure measurement using an occlusion cuff typically takes twenty to sixty seconds. An important factor that influences the accuracy of all indirect blood-pressure measurement methods that utilize an occlusion cuff is the assumption that the living subject's blood pressure remains constant during the measurement. However, a living subject's physiologic state can change significantly over the indirect blood-pressure measurement time, particularly if the living subject is a surgical or critical care patient that is suffering from advanced cardiovascular disease, respiratory disease, kidney disease or blood loss. The change in the living subject's cardiovascular state may be due to changes in heart rate, cardiac output, vasomotor tone or circulating blood volume.

Changes in the living subject's blood pressure during the blood-pressure measurement will distort the amplitude envelope of the pressure pulses produced in the occlusion cuff as the pressure applied by the cuff passes through the blood-pressure pulse range. The distortion of the amplitude envelope will result in a shifting of the amplitude envelope features associated with the living subject's systolic, diastolic and mean blood pressures. This is particularly true for oscillometric blood-pressure measurement devices that analyze the entire amplitude envelope of the pressure pulses.

If the living subject's blood pressure is changing during the blood-pressure measurement, the time delay between the measurement of the subject's systolic blood pressure and the measurement of the subject's diastolic blood pressure results in an erroneously high measured pulse pressure or an erroneously low measured pulse pressure. As shown in FIG. 1, if the living subject's blood pressure is falling during the blood-pressure measurement, the measured systolic blood pressure $S_M$ is higher than the living subject's true systolic blood pressure $S_T$ when the living subject's measured diastolic blood pressure $D_M$ is measured. As a result, the measured pulse-pressure $PP_M$ is greater than the living subject's actual pulse-pressure $PP_T$. If the living subject's blood pressure is rising during the blood-pressure measurement, the opposite effect occurs. In either case, the erroneous blood pressure values may mislead or confuse a living subject's caregiver.

Another phenomenon that can cause the living subject's blood pressure to change during the blood-pressure measurement is an abnormal heartbeat, commonly referred to as an arrhythmia. Arrhythmias are common in critically ill patients and result when the living subject's heart contracts earlier or later than normal. Arrhythmias can also result when the heart contracts with increased or decreased strength.

Arrhythmias can be produced by a number of abnormalities in the electromyocardial conduction system. The physiologic events that cause arrhythmias originate in the heart rather than the central nervous system.

Arrhythmias can be easily identified in an electrocardiogram by comparing the inter-beat interval time of successive heartbeats and the morphology of the electrocardiogram complex. However, arrhythmias are difficult to identify in other physiologic signals, such as an oscillometric pulse signal. This is because the oscillometric pulse signal is sensitive to environmental noise and motion artifacts, e.g., movement of the living subject during a blood-pressure measurement. Environmental noise or motion artifacts can produce pulses that are similar to the pulses produced by arrhythmias.

Most blood-pressure measurement devices exclude arrhythmias from the oscillometric blood-pressure measurement for two reasons. First, most blood-pressure measurement devices cannot reliably differentiate an arrhythmia from an environmental or motion artifact that should be deleted from the data set. Second, blood-pressure pulses produced by arrhythmias alter oscillometric pulse amplitudes. The altered oscillometric pulse amplitudes distort the amplitude envelope of the pulses used for measuring the living subject's blood-pressure.

In blood-pressure measurement devices that utilize a step-wise deflation cuff, multiple pulses are detected at each cuff pressure level until a non-arrhythmic pulse is detected. This method can lead to excessively long measurement times if the living subject's heart exhibits frequent arrhythmias. In blood-pressure measurement devices that utilize a continuous-deflation cuff, arrhythmic pulses are rejected and extrapolation is used to fill in the missing data point. This method results in a data set with lower resolution and a decrease in the accuracy of the blood-pressure measurement. The effect of arrhythmias on the accuracy of the blood-pressure measurement is dependent upon the relationship of the arrhythmia to the systolic, diastolic and mean blood-pressure detection points.

Other conditions can also result in less accurate or misleading blood-pressure measurements. For example, the ultimate accuracy of an indirect blood-pressure measurement is dependent upon the change in cuff pressure between detected heartbeats. If the living subject's heart rate is very low relative to the cuff's deflation rate, a large change in cuff pressure will occur between heartbeats. This reduces the accuracy of the blood-pressure measurement. In addition, if the living subject is in shock, the living subject's blood-pressure pulses, and the resulting measured oscillometric pulses, are too low for identification of the blood-pressure features in the amplitude envelope of the oscillometric pulses. If the living subject is restless, shivering or otherwise moving, there may be too many motion artifacts to make a blood-pressure measurement.

Most blood-pressure measurement devices make several attempts to measure the living subject's blood pressure before they sound an alarm. In this situation, the monitoring of the living subject's condition is interrupted while a user corrects the problem.

SUMMARY OF THE INVENTION

This invention provides a blood-pressure measurement system that accurately monitors a living subject's cardiovascular state, even if the living subject's blood pressure changes during a measurement, the living subject exhibits frequent arrhythmias, or motion artifacts are present during the blood-pressure measurement. The blood-pressure measurement system of this invention provides an arrhythmia-pulse correcting circuit that corrects the amplitudes of oscillometric pulses produced by arrhythmias. Thus, the arrhythmic pulses may be retained for use in determining the living subject's blood pressure. An oscillometric-systolic-pressure correcting circuit corrects the measured systolic oscillometric blood pressure when a living subject's blood pressure is changing during the oscillometric blood-pressure measurement. A quality-assurance and data-checking circuit determines the reliability of the oscillometric blood-pressure values, determines the cause of problems in the blood-pressure measurement process, alerts a user if a reliable oscillometric blood-pressure measurement cannot be obtained and performs user-specified living subject evaluation checks.

In a preferred embodiment, the blood-pressure measurement system of this invention provides an electrocardiographic-waveform detection device that detects an electrocardiographic waveform generated by the change in electric potential of the living subject's cardiac muscle. A pulse-period measuring circuit determines the living subject's pulse period between predetermined periodic reference points on successive electrocardiographic waveforms.

The blood-pressure measurement system also provides an oximeter sensor to detect the living subject's pulse wave. A pulse-wave-area determining device analyzes the pulse waveform obtained from the oximeter sensor and determines pulse-wave areas, including an oximeter pulse amplitude, that are used in identifying abnormal waveforms.

A pulse-wave-propagation-information obtaining circuit determines the amount of time it takes a pulse wave to propagate from the living subject's heart to the oximeter sensor based on the oximeter pulse signal and the electrocardiographic waveforms. The pulse-wave-propagation-information obtaining circuit also determines the velocity of the pulse wave.

A blood-pressure/pulse-wave-propagation-information-relationship determining circuit determines and calibrates a relationship between the pulse wave propagation time and the living subject's blood pressure. A relationship correcting circuit corrects the blood-pressure/propagation-time relationship based on the living subject's heart rate measured by the heart-rate measuring circuit. An estimated-blood-pressure determining circuit estimates the blood pressure associated with each heartbeat based on the determined pulse-wave propagation time and the blood-pressure/propagation-time relationship.

A blood-pressure-measurement starting circuit initiates a new oscillometric blood-pressure measurement when the estimated blood pressure, pulse-period abnormalities and pulse-wave-area abnormalities meet certain predetermined criteria.

These and other features and advantages of this invention are described in or are apparent from the following detailed description of the preferred embodiments.

BRIEF DESCRIPTION OF THE DRAWINGS

The preferred embodiments of this invention will be described in detail, with reference to the following figures, wherein:

FIGS. 5A–5C are a block diagram of an electronic control device of the blood-pressure measurement system of FIG. 2;

FIGS. 10A and 10B show a flowchart of a preferred control subroutine for measuring a living subject's blood pressure;

DETAILED DESCRIPTION OF PREFERRED EMBODIMENTS

Figure 1:
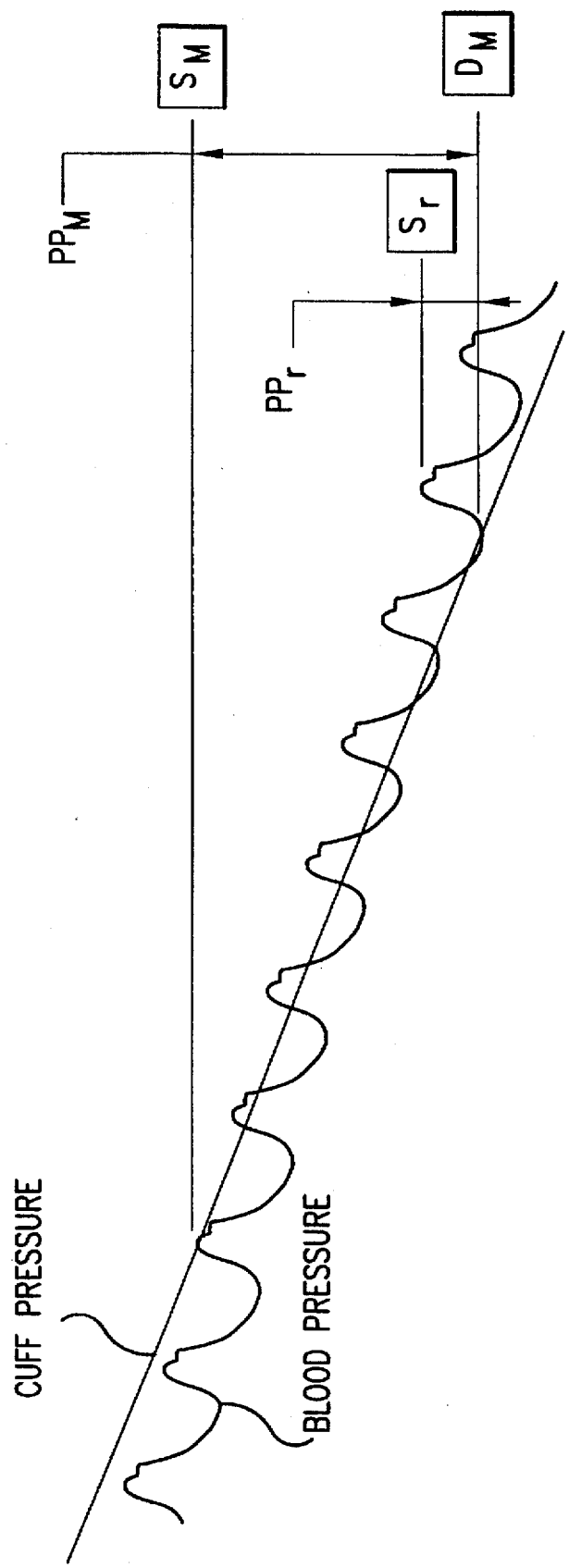
FIG. 1 shows a blood-pressure measurement while a living subject's blood pressure is changing.
Figure 2:
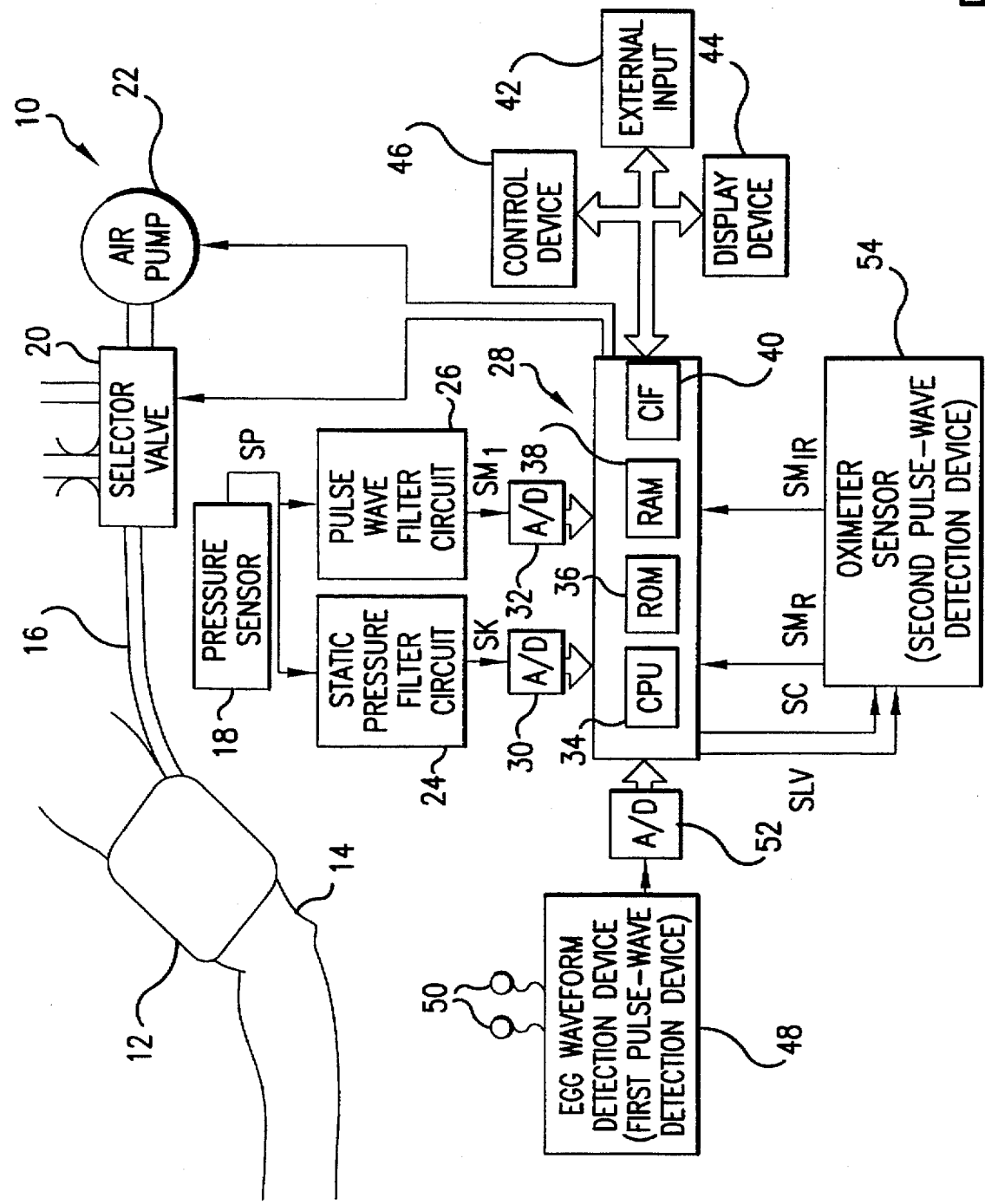
FIG. 2 is a combined schematic and block diagram of the blood-pressure measurement system of this invention.

FIG. 2 shows one embodiment of the blood-pressure measurement system 10 of this invention. The system 10 includes an inflatable cuff 12 which is preferably formed by a rubber bag that is positioned inside a flexible cloth bag. The inflatable cuff 12 is wrapped around a portion of a living subject, e.g., an upper arm 14 of a subject.

The inflatable cuff 12 is connected via piping 16 to a pressure sensor 18, a selector valve 20 and an air pump 22. The selector valve 20 is selectively placeable in either an inflation position, a slow-deflation position or a quick-deflation position. In the inflation position, the selector valve 20 allows pressurized air from the air pump 22 to be supplied to the inflatable cuff 12. In the slow-deflation position, the selector valve 20 allows the pressurized air in the inflatable cuff 12 to be slowly discharged. In the quick-deflation position, the selector valve 20 allows the pressurized air in the inflatable cuff 12 to be quickly discharged.

The pressure sensor 18 detects an air pressure in the inflatable cuff 12 and supplies a pressure signal SP, representing the detected pressure, to a static-pressure filter circuit 24 and a pulse-wave filter circuit 26. The static-pressure filter circuit 24 includes a low-pass filter that extracts a static component contained in the pressure signal SP, i.e., a cuff pressure signal SK that represents the static cuff pressure. The cuff pressure signal SK is supplied to an electronic control device 28 via a first A/D converter 30.

The pulse-wave filter circuit 26 includes a band-pass filter that extracts an oscillatory component of the pressure signal SP falling within a predetermined frequency range. The oscillatory component is supplied as a cuff pressure signal $SM_1$ to the electronic control device 28 via a second A/D converter 32. The cuff pressure signal $SM_1$ represents an oscillatory pressure wave that is produced from a peripheral artery, preferably a brachial artery, of the subject and that propagates to the area on the subject's limb, preferably an upper portion of a right arm 14, in contact with the inflatable cuff 12.

The electronic control device 28 preferably includes a central processing unit (CPU) 34, a read-only memory (ROM) 36, a random-access memory (RAM) 38 and a communication interface (CIF) 40. The CPU 34 processes input signals according to control programs stored in the ROM 36 using the RAM 38 as temporary storage. In addition, the CPU 34 transmits and receives information from other instruments, computers and monitors through the communication interface 40 and external inputs 42. The CPU 34 also outputs display signals to a display device 44 through the communication interface 40 and receives information from control devices 46, e.g., switches, keyboards, touch screens, etc., through the communication interface 40.

When a blood-pressure measurement is initiated, the CPU 34 supplies a control signal to the selector valve 20 to place it in the inflation position and a drive signal to the air pump 22 to inflate the inflatable cuff 12, thus compressing the upper portion of the subject's right arm 14. The CPU 34 then supplies a control signal to the selector valve 20 to place it in the slow-deflation position, thus gradually reducing the air pressure in the inflatable cuff 12.

While the air pressure in the inflatable cuff 12 is gradually reduced, the CPU 34 obtains the pulse-wave pressure signal $SM_1$ and the cuff pressure signal SK from the pressure sensor 18 via the pulse-wave filter circuit 26 and the static-pressure filter circuit 24, respectively. The CPU 34 then determines the subject's systolic blood-pressure value SBP, the subject's diastolic blood-pressure value DBP and the subject's mean blood-pressure value $BP_{mean}$ based on the obtained signals $SM_1$ and SK using well-known oscillometric blood-pressure measuring techniques. These techniques are based on the variation of the amplitudes of the heartbeat-synchronous pulses of the oscillatory pressure-pulse wave (i.e., the pulse-wave pressure signal $SM_1$).

The blood-pressure measurement system 10 also includes an electrocardiographic-waveform detection device 48. The electrocardiographic-waveform detection device 48 continuously detects an electrocardiographic waveform that indicates the change in electric potential of the subject's cardiac muscle. The electrocardio-graphic-waveform detection device 48 determines the electrocardiographic waveform from signals supplied by multiple electrodes 50. The electrodes 50 are placed at predetermined positions on the living subject. The electrocardiographic waveform detection device 48 is suitably an electrocardiograph, and the electrocardio-graphic-waveform is suitably an electrocardiogram detected by the electrocardiograph.

The electrocardiographic-waveform detection device 48 supplies the electrocardographic waveform to the electronic control device 28 via a third A/D converter 52. The display device 44 may optionally record the electrocardiographic waveform on a recording sheet (not shown). The electrodiographic-waveform detection device 48 also functions as a first pulse-wave detection device that detects pulse waves from a first portion of the living subject, as will be explained in more detail below.

Figure 3:
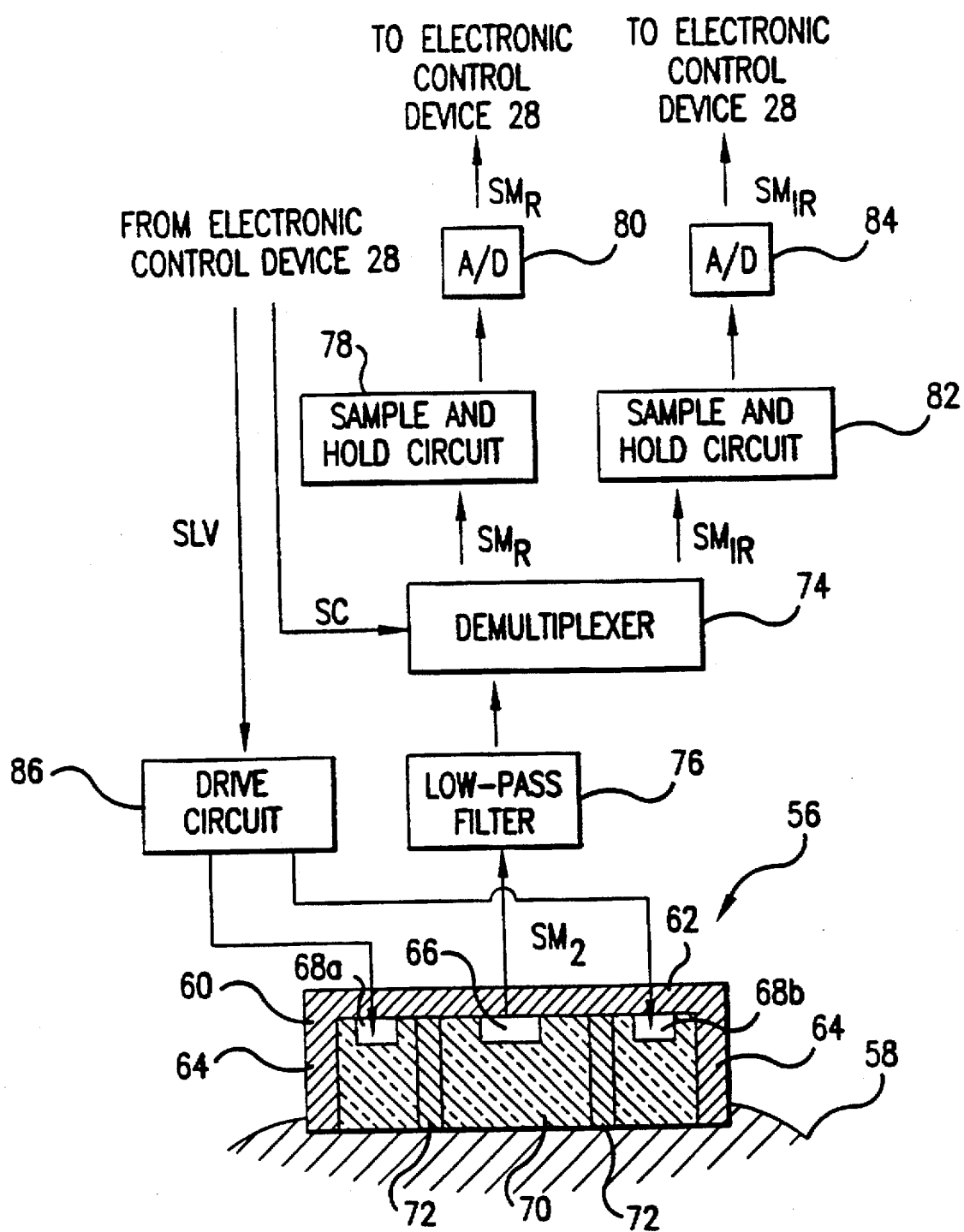
FIG. 3 is a combined schematic and block diagram of a first preferred embodiment of an oximeter sensor of the blood-pressure measurement system of FIG. 2.

The blood-pressure measurement system 10 also includes an oximeter sensor 54. A first preferred embodiment of the oximeter sensor 54 is shown in FIG. 3.

The oximeter sensor 54 preferably comprises a photoelectric pulse-wave detector 56. The photoelectric pulse-wave detector 56 is tightly attached to the surface 58 of the subject. The photoelectric pulse-wave detector 56 is preferably attached to the tip of a finger of the living subject, preferably with bands (not shown).

The photoelectric pulse-wave detector 56 has a container-like housing 60 that has a top portion 62, side portions 64 and an open bottom. A photodetector 66 is attached to the bottom surface of the top portion 62. The photodetector 66 is preferably centered on the top portion 62 of the housing 60.

A first group of light emitters 68a and a second group of light emitters 68b are attached to the bottom surface of the top portion 62 alternately around the photodetector 66. The first group of light emitters 68a preferably emit red light at a wavelength of approximately 660 nm and the second group of light emitters 68b preferably emit infrared light at a wavelength of approximately 800 nm.

A transparent resin 70, which is preferably an acrylic resin, fills the inside of the housing 60 and encases the photodetector 66 and the light emitters 68a and 68b. A light shield 72, which is preferably a metal plate, is positioned inside the housing 60 to shield the photodetector 66 from light reflected directly towards the photodetector 66 by the surface 58.

In operation, the groups of light emitters 68a and 68b are turned on and off in an alternating fashion at a predetermined frequency. Thus, only one of the two light emitter groups 68a and 68b is on at any given time. Light emitted by either the light emitters 68a or the light emitters 68b impinges on and penetrates into the surface 58 of the living subject and is dispersed by the hemoglobin in the capillaries in the living subject. A portion of the dispersed light is detected by the photodetector 66.

Although the first group of light emitters 68a emit light at a preferred wavelength of 660 nm, other wavelengths may be used so long as, at the selected wavelength, the absorption coefficient of oxidized hemoglobin is substantially different than the absorption coefficient of reduced hemoglobin.

The photodetector 66 detects a portion of the light dispersed by capillaries that are close to the surface 58 of the living subject and outputs a pulse wave signal $SM_2$ whose magnitude is proportional to the amount of light detected. The pulse wave signal $SM_2$ is input to a demultiplexer 74 via a low-pass filter 76.

In operation, the CPU 34 sends a drive signal SLV to the light emitters 68a and 68b of the photoelectric pulse-wave detector 56 via the drive circuit 86. As discussed above, the CPU 34 controls the light emitters 68a and 68b to alternately emit light.

The low-pass filter 76 removes high frequency noise from the pulse wave signal $SM_2$. If necessary, an amplifier (not shown) may be used between the photodetector 66 and the low-pass filter 76.

The demultiplexer 74 is synchronized with the drive circuit 86 and the photoelectric pulse-wave detector 56. Thus, the demultiplexer 74 alternately supplies red light signals $SM_R$, via a sample and hold circuit 78 and a fourth A/D converter 80, and infrared light signals $SM_{IR}$, via a sample and hold circuit 82 and a fifth A/D converter 84, to an input/output port of the electronic control device 28. The CPU 34 routes the signal $SM_R$ to the sample and hold circuit 78 and the signal $SM_{IR}$ to the sample and hold circuit 82 by sending a switching signal SC to the demultiplexer 74. The sample and hold circuits 78 and 82 hold the current $SM_R$ and $SM_{IR}$ signals until the previous $SM_R$ and $SM_{IR}$ are processed by the electronic control device 28.

The CPU 34 determines a level of hemoglobin oxygen saturation in the living subject's blood based on the amplitudes of the signals $SM_R$ and $SM_{IR}$. The CPU 34 determines the level of hemoglobin oxygen saturation using predetermined programs stored in the ROM 36. One method of determining the level of hemoglobin oxygen saturation is disclosed in U.S. Pat. No. 5,131,391. The photoelectric pulse-wave detector 56 also functions as a second pulse-wave detection device, as will be explained in more detail below.

Figure 4:
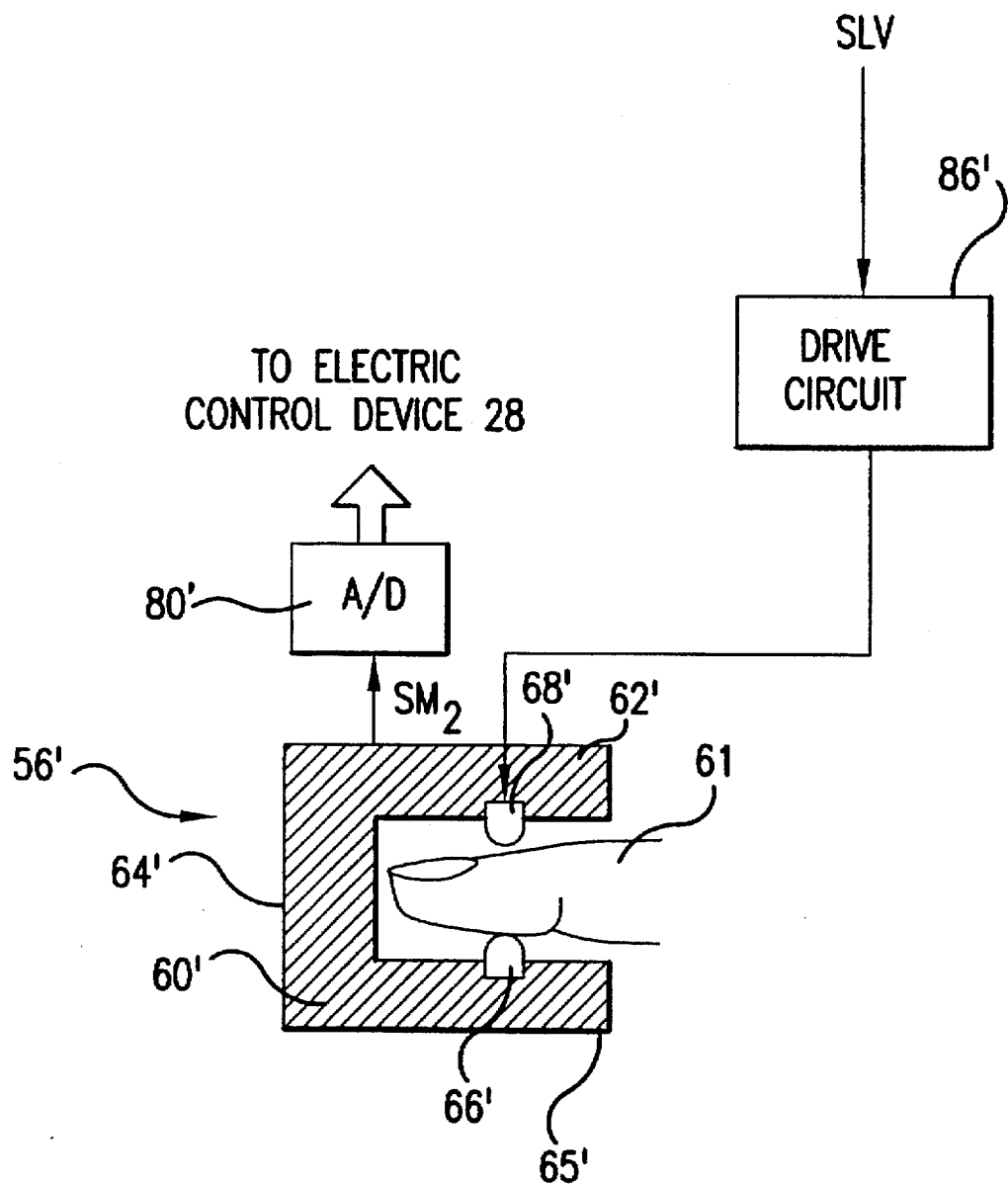
FIG. 4 is a combined schematic and block diagram of a second preferred embodiment of an oximeter sensor of the blood-pressure measurement system of FIG. 2.

FIG. 4 shows a second preferred embodiment of the oximeter sensor 54. The second preferred oximeter embodiment comprises a photoelectric pulse-wave detector 56'.

The photoelectric pulse-wave detector 56' has a housing 60' that can accommodate a body portion, e.g., a finger 61. The housing 60' has a top portion 62', a side portion 64' and a bottom portion 65'. A photodetector 66' and a light emitter 68' are attached to opposite inside surfaces of the housing 60'. The photodetector 66' is preferably attached to the inside surface of the bottom portion 65' and the light emitter 68' is preferably attached to the inside surface of the top portion 62'.

The light emitter 68' preferably emits red light at a wavelength of approximately 660 nm. However, the light emitter 68' may emit light at other wavelengths so long as the emitted wavelength is reflected by the hemoglobin present in the blood.

In operation, the CPU 34 sends a drive signal SLV to the light emitter 68' of the photoelectric pulse-wave detector 56' via the drive circuit 86'. Light emitted by the light emitter 68' that is not reflected by the hemoglobin present in the blood flowing through the finger 61 is detected by the photodetector 66'.

The photodetector 66' outputs a pulse wave signal $SM_2$ whose magnitude is proportional to the amount of light transmitted through the finger 61 and detected by the photodetector 66'. The amount of light transmitted through the finger 61 is represents the instantaneous amount of hemoglobin in the finger 61, i.e., the instantaneous blood volume in the finger 61. Thus, the pulse wave signal $SM_2$ oscillates or pulsates in synchronism with the heartbeat of the living subject. Accordingly, the photoelectric pulse-wave detector 56' functions as a second pulse-wave detection device. The pulse wave signal $SM_2$ is input to the electronic control device 28 via an A/D converter 80'.

In addition to functioning as a second pulse-wave detection device, the photoelectric pulse-wave detector 56' also functions as an oximeter. The CPU 34 determines a level of hemoglobin oxygen saturation in the living subject's blood based on the amplitude of the signal $SM_2$. The CPU 34 determines the level of hemoglobin oxygen saturation using predetermined programs stored in the ROM 36.

Figure 5A:
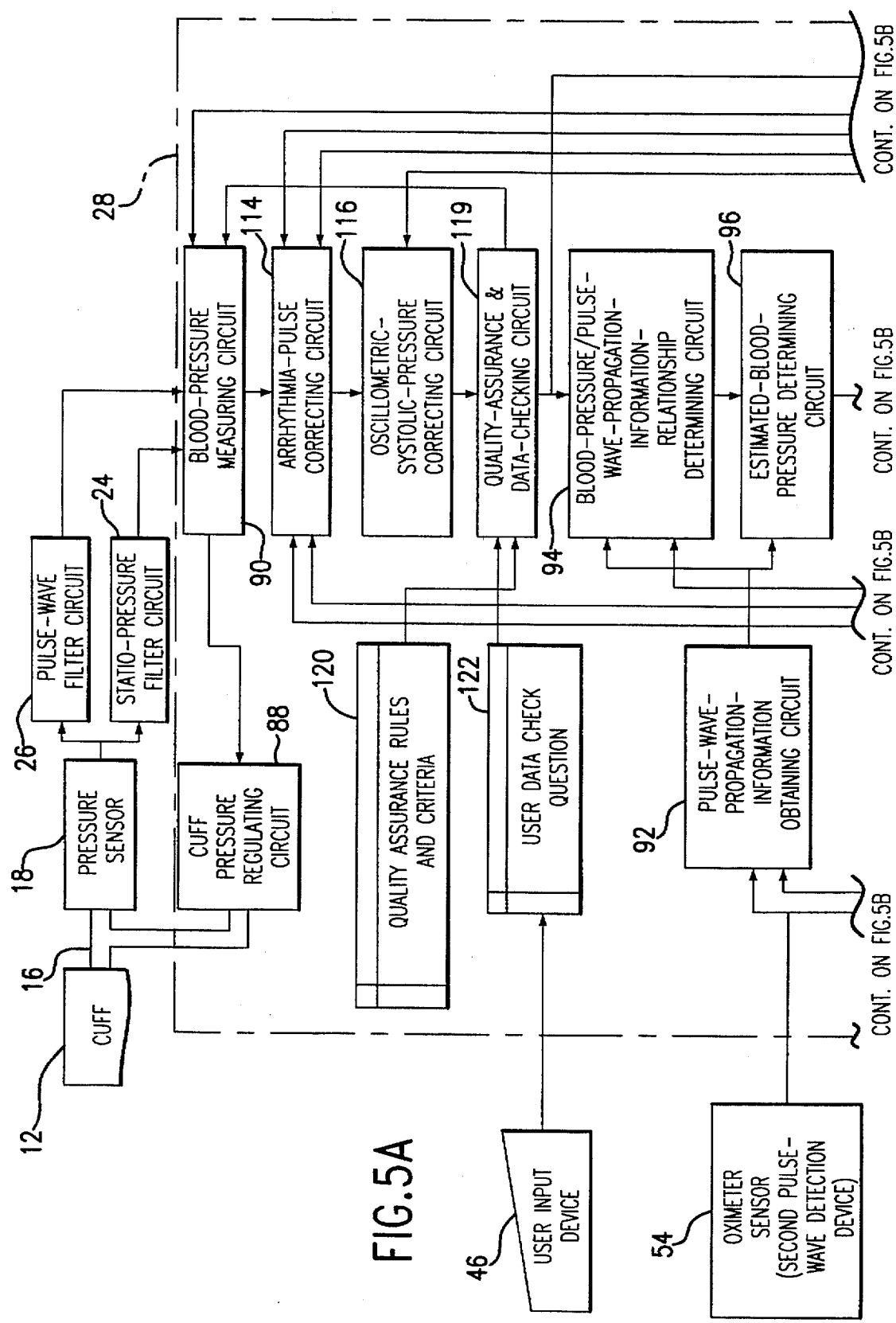
Figure 5B:
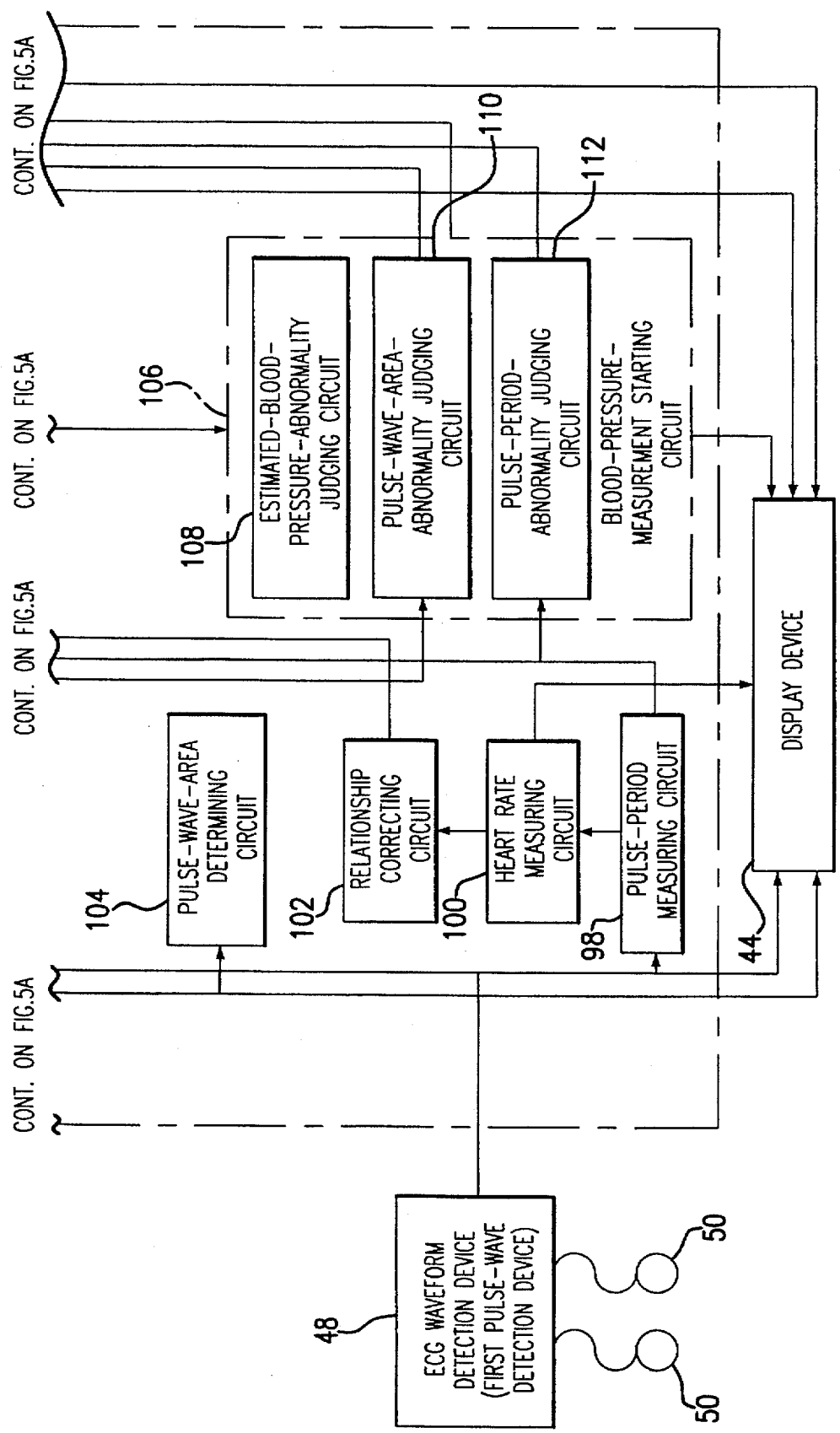

FIGS. 5A–5B show the control functions of the electronic control device 28 of the blood-pressure measurement system 10 of this invention.

The electronic control device 28 regulates the air pressure in the inflatable cuff 12 via a cuff-pressure regulating circuit 88. When a blood-pressure measurement is initiated, the cuff-pressure regulating circuit 88 switches the selector valve 20 to the inflation position and drives the air pump 22 to quickly increase the air pressure in the inflatable cuff 12 to a predetermined target value, e.g., 180 mmHg. If the living subject's blood-pressure has been recently measured, the cuff-pressure regulating circuit 88 will inflate the inflatable cuff 12 to a pressure suitably above the previously measured systolic blood-pressure, e.g., 30 mmHg above the previously measured systolic blood-pressure. Subsequently, the cuff-pressure regulating circuit 88 switches the selector valve 20 to a slow-deflation position to slowly decrease the air pressure in the inflatable cuff 12, preferably at a rate of approximately 3 mmHg/sec.

While the air pressure in the inflatable cuff 12 is slowly decreasing, a blood-pressure measuring circuit 90 uses a well-known oscillometric method to measure the subject's systolic blood pressure, diastolic blood pressure and mean blood pressure. The blood-pressure measurements are based on the variation in the amplitudes of the heartbeat-synchronous pulses of the oscillatory pressure-pulse waves (i.e., of the cuff oscillatory pressure-pulse-wave signal $SM_1$) obtained through the pulse-wave filter circuit 26 while the air pressure in the inflatable cuff 12 slowly decreases.

Figure 6:
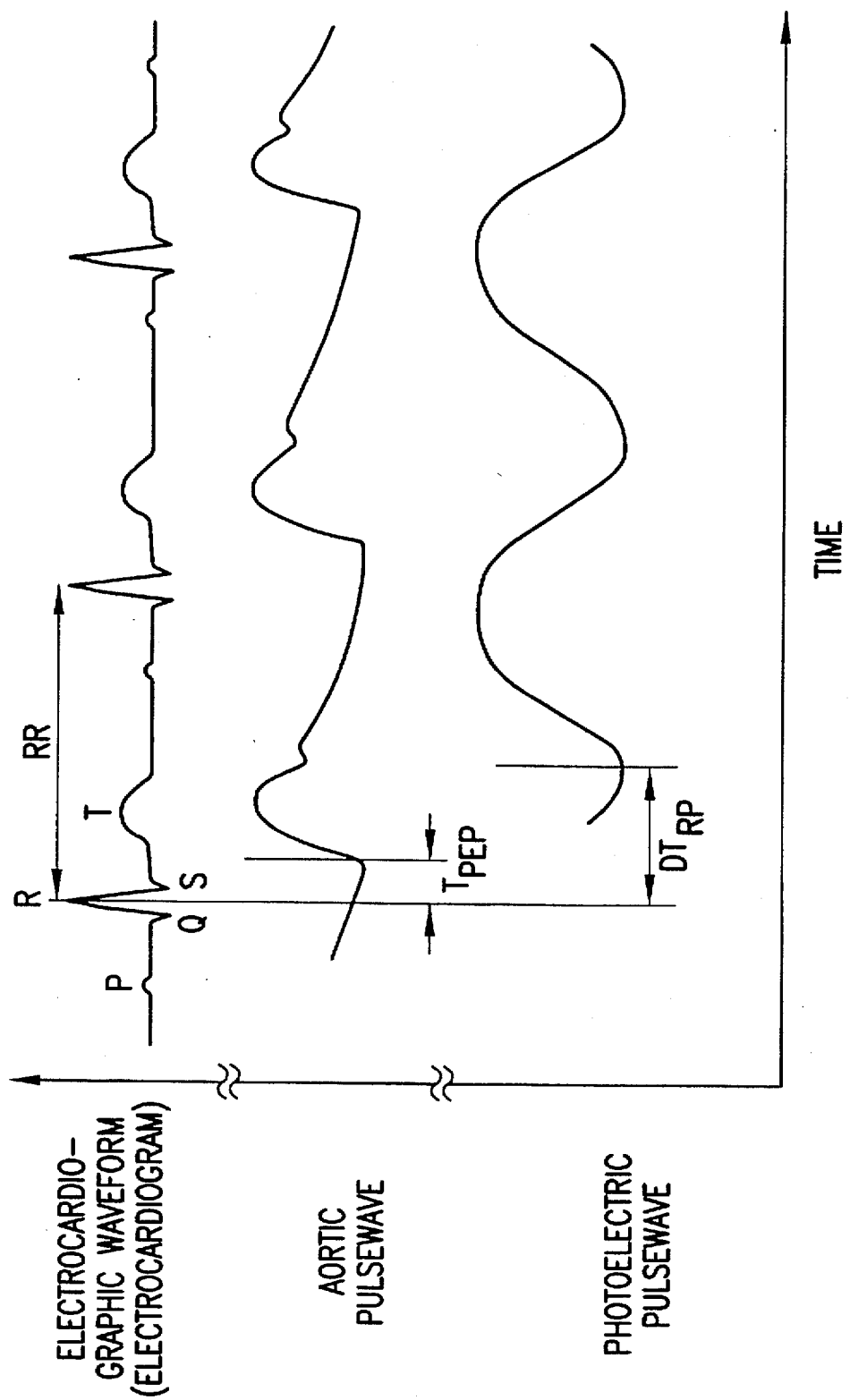
FIG. 6 is a timing chart of the blood-pressure measurement system of FIG. 2.

A pulse-wave propagation-information obtaining circuit 92 includes a time-difference determining circuit (not shown). The time-difference determining circuit determines a pulse-wave propagation time $DT_{RP}$ by determining a time difference between a predetermined periodic point on the electrocardiographic waveform of each of the periodic pulses successively detected by the electrocardiographic-waveform detection device 48 and a predetermined periodic point on the waveform of a corresponding one of the periodic pulses detected by the photoelectric pulse-wave detector 56 of the oximeter sensor 54. In the preferred embodiment, the pulse-wave propagation-information obtaining circuit 92 determines the time difference $DT_{RP}$ between an R point on the electrocardiographic waveform and a minimum point of the photoelectric pulse-wave detected by the photoelectric pulse-wave detector 56, as shown in FIG. 6.

The pulse-wave propagation-information obtaining circuit 92 further determines a pulse-wave propagation velocity $V_M$ (m/sec) of the pulse wave propagating through the artery of the subject, based on the determined pulse-wave propagation time $DT_{RP}$, according to the expression:

$$V_M = L/(DT_{RP} - T_{PEP}) \tag{1}$$

where:

L is the length of the living subject's artery from the left ventricle to the point where the photoelectric pulse-wave detector 56 is positioned on the living subject via the aorta and other peripheral arteries; and $T_{PEP}$ is the pre-ejection period between an R wave of the electrocardiographic waveform and a minimum point (i.e., rising point) of the aortic pulse wave waveform.

A blood-pressure/pulse-wave-propagation-information-relationship determining circuit 94 determines, in advance, a relationship between an estimated systolic blood-pressure value $EBP_{SYS}$ and either the pulse-wave propagation time $DT_{RP}$ or the pulse-wave propagation velocity $V_M$ according to the expressions:

$$EBP_{SYS}=A(DT_{RP})+B; \text{ and} \qquad (2)$$

$$EBP_{SYS}=C(V_M)+D \qquad (3)$$

where:

A is a negative constant; and

B, C and D are positive constants.

Equation (2) shows a relationship between systolic blood-pressure SBP and pulse-wave propagation time $DT_{RP}$. Equation (3) shows a relationship between systolic blood-pressure SBP and pulse-wave propagation velocity $V_M$. Alternatively, the blood-pressure/pulse-wave-propagation-information-relationship determining circuit 94 may determine a relationship between a mean blood-pressure $BP_{MEAN}$ or a diastolic blood-pressure DBP determined by the blood-pressure measuring circuit 90 and either the pulse-wave propagation time $DT_{RP}$ or the pulse-wave propagation velocity $V_M$. Generally, the particular type of blood-pressure/pulse-wave-propagation-information relationship that is determined is dependent upon which of the systolic blood-pressure value, mean blood-pressure value or diastolic blood-pressure value is selected as the estimated blood-pressure value EBP.

An estimated-blood-pressure determining circuit 96 successively determines, based on the relationship determined by the blood-pressure/pulse-wave-propagation-information-relationship determining circuit 94, an estimated blood-pressure value EBP for the living subject. The estimated-blood-pressure determining circuit 96 preferably determines an estimated systolic blood-pressure value $EBP_{SYS}$. The estimated systolic blood-pressure values $EBP_{SYS}$ determined by the estimated-blood-pressure determining circuit 96 are continuously output to the display device 44. The display device 44 successively displays the estimated systolic blood-pressure values $EBP_{SYS}$ for each heartbeat synchronous pulse.

A pulse-period measuring circuit 98 determines a pulse period RR by measuring a time difference between predetermined periodic points on two successive pulses of the electrocardiographic waveform detected by the electrocardiographic-waveform detection device 48. In the preferred embodiment, the pulse-period measuring circuit 98 determines a time difference between the R points of two successive pulses of the electrocardiographic wave-form.

A heart-rate measuring circuit 100 determines the living subject's heart rate based on the pulse period determined by the pulse-period measuring circuit 98. A relationship correcting circuit 102 makes corrections to the blood-pressure/pulse-wave-propagation relationship determined by the blood-pressure/pulse-wave-propagation-information-relationship determining circuit 94 based on the heart rate determined by the heart-rate measuring circuit 100 and a predetermined correction factor.

A pulse-wave-area determining circuit 104 determines a pulse-wave area VR by normalizing an area S defined by the waveform of each pulse of the photoelectric pulse-wave detected by the photoelectric pulse-wave detector 56, based on a period W and an amplitude L of the pulse of the photoelectric pulse-wave.

Figure 7:
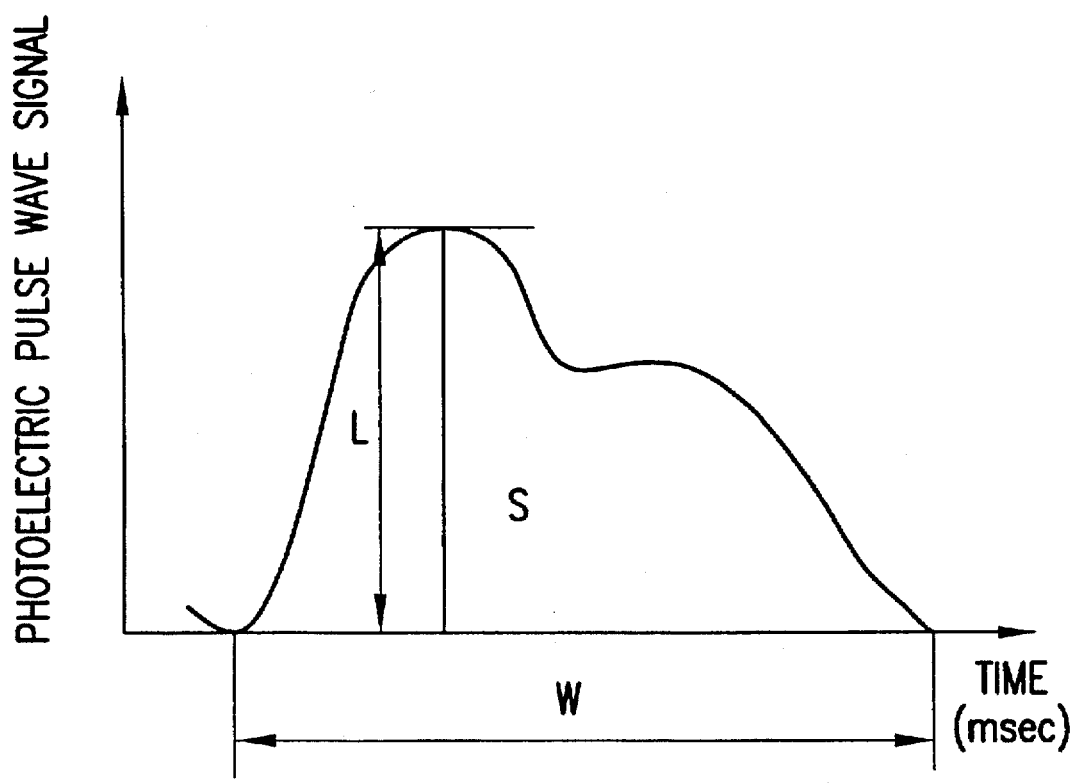
FIG. 7 shows a photoelectric pulse-wave signal detected by the oximeter sensor of FIG. 3.

As shown in FIG. 7, the waveform of each pulse of the photoelectric pulse-wave is defined by a series of data points, representing respective pulse magnitudes, which are input at a predetermined interval, e.g., several milliseconds. The pulse-wave area S is obtained by integrating, over the period W of the pulse, the respective magnitudes of the data points input over the predetermined interval. The normalized pulse-wave area VR is obtained with the expression:

$$VR=S/(W \times L) \qquad (4)$$

where L is the photoelectric pulse amplitude. The normalized pulse-wave area VR is a dimensionless value that indicates the ratio of the pulse-wave area to an area defined by the photoelectric pulse period W and the photoelectric pulse amplitude L.

A blood-pressure-measurement starting circuit 106 comprises an estimated-blood-pressure-abnormality judging circuit 108, a pulse-wave-area-abnormality judging circuit 110 and a pulse-period-abnormality judging circuit 112.

The estimated-blood-pressure-abnormality judging circuit 108 determines that the estimated systolic blood-pressure value $EBP_{SYS}$, determined by the estimated-blood-pressure determining circuit 96, is abnormal when the estimated systolic blood-pressure value $EBP_{SYS}$ deviates by a predetermined amount from the last systolic blood-pressure value measured by the blood-pressure measuring circuit 90 using the inflatable cuff 12.

The pulse-wave-area-abnormality judging circuit 110 determines that a pulse-wave area VR determined by the pulse-wave-area determining circuit 104 is abnormal when the pulse-wave area VR deviates by a predetermined amount from a pulse-wave area determined in the previous blood-pressure measurement using the inflatable cuff 12.

The pulse-period-abnormality judging circuit 112 determines that a pulse period RR determined by the pulse-period measuring circuit 98 is abnormal when the pulse period RR deviates by a predetermined amount from a pulse period determined in the previous blood-pressure measurement using the inflatable cuff 12. In the preferred embodiment, the blood-pressure-measurement starting circuit 106 initiates a new blood-pressure measurement with the blood-pressure measuring circuit 90 when: 1) the estimated systolic blood-pressure value $EBP_{SYS}$ is determined to be abnormal; 2) and when either the pulse period RR or the pulse-wave area VR is determined to be abnormal.

An arrhythmia-pulse correcting circuit 114 corrects the amplitude of oscillometric pulses that are produced by arrhythmias so they can be used during an oscillometric blood-pressure measurement.

As discussed above, arrhythmias are primarily related to the disruption of the myoelectric processes of the heart. Arrhythmias are manifested in the electrocardiographic waveform as shortened or lengthened beat-to-beat intervals and as alterations in the shape of the electrocardiographic waveform. With some types of arrhythmias, e.g., a pre-ventricular contraction, the abnormal beat occurs earlier than normal and the following beat, whether it is a normal beat or an arrhythmia, is delayed. In order to utilize an oscillometric pulse produced by an arrhythmia, any alterations in the subject's blood-pressure produced by the arrhythmic pulse must be corrected.

Arrhythmias can result in a greater or lesser volume of blood, i.e., a greater or lesser stroke volume, being injected into the arterial system than would be injected during a normal beat. Near the heart, the aortic blood-pressure $P_A(t)$ produced by the stroke volume of a heartbeat is dependent upon the pressure at the start of the beat, the volumetric flow produced by the heart $Q_A(t)$ and the total impedance $Z_S$ of the vascular system. The relationship is given by:

$$P_A(t) = Z_S Q_A(t). \tag{5}$$

The vascular impedance is governed by the compliance and resistance of the arterial tree, and the blood's inertia. The aortic blood-pressure $P_A(t)$ is composed of the mean or average blood-pressure $BP_{MEAN}$ and a time-varying blood-pressure $P_P(t)$, according to the following relation:

$$P_A(t) = BP_{MEAN} + P_P(t). \tag{6}$$

The mean blood-pressure $BP_{MEAN}$ is primarily dependent upon the cardiac output and the total peripheral resistance of the arterial tree. The amplitude of the time-varying blood-pressure $P_P(t)$ is commonly known as the pulse-pressure. For a given heartbeat, the mean cardiac output is simply the stroke volume divided by the duration of the pulse. Therefore, the mean pressure of a blood-pressure pulse, assuming steady-state conditions, is given by:

$$BP_{MEAN} = R_p \Delta V_s / \Delta t_b \tag{7}$$

where:

$BP_{MEAN}$ is the mean aortic blood-pressure;

$R_p$ is the total peripheral resistance of the arterial tree;

$\Delta V_s$ is the stroke volume; and $\Delta t_b$ is a duration of the pulse.

The pulse pressure and the shape of the pulse wave is dependent upon the stroke volume and both the compliance and the resistance of the arterial tree. In generally stable living subjects, the resistance and compliance of the arterial tree tend to change slowly unless a special situation occurs, e.g., the cutting of a major vessel that produces massive hemorrhaging. Therefore, on a beat-to-beat basis, both the pulse pressure and the mean blood pressure are primarily dependent upon the volume of blood ejected by the last heart contraction.

The difference in stroke volume produced by an arrhythmia is a result of a prolonged or reduced filling time, or a reduced contractile strength of the heart. If the stroke volume is increased, the blood pressure is increased. Similarly, if the stroke volume is reduced, the resulting blood pressure is also reduced. Furthermore, if the heartbeat occurs earlier than normal, the resulting blood pressure may be higher than at the start of a normal heartbeat.

Even though the stroke volume of an early heartbeat may be reduced, the resulting abnormal pulse will begin at a higher pressure than a normal pulse, resulting in a higher peak pressure. Conversely, if the abnormal heartbeat is delayed, resulting in increased filling time and greater stroke volume, the blood pressure may have fallen sufficiently to make the sum of the volume pulse pressure and the lower starting (diastolic) blood pressure less than that produced by a normal heartbeat.

When the blood pressure of a living subject is measured on the upper arm with an occlusion cuff, the measured blood pressure is that of the brachial artery, which can be different than the blood pressure in the aorta. The blood pressure at any given location in the arterial tree is dependent upon the central aortic pressure and the impedance distribution of the vascular system.

Figure 8:
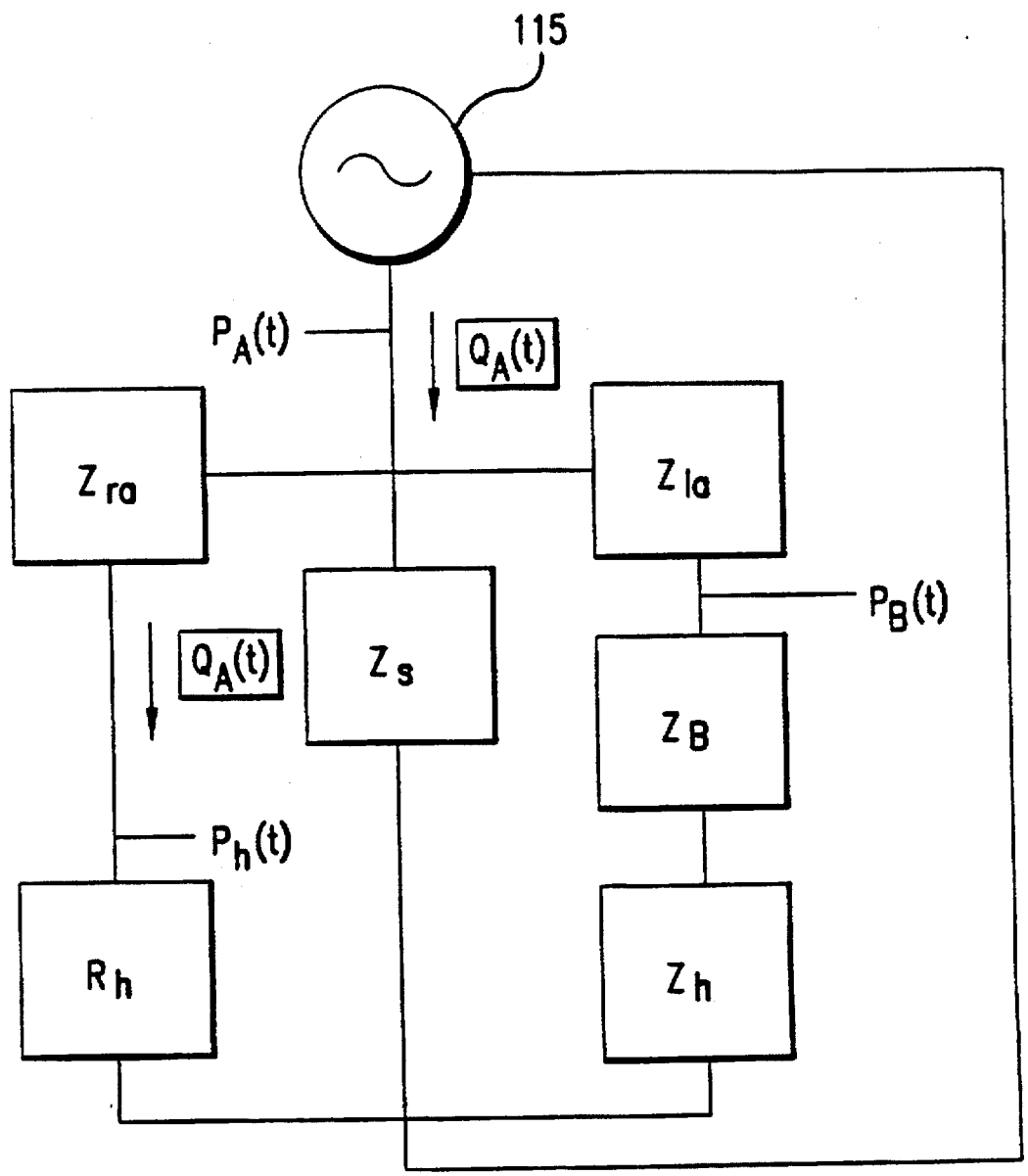
FIG. 8 is a schematic diagram of a living subject's blood circulatory system.

As shown in FIG. 8, the vascular system can be modeled as a pump 115, i.e., the heart, that produces a periodic blood flow $Q_A(t)$ at an aortic pressure $P_A(t)$ that is distributed to the right arm, left arm and the remainder of the living subject's body. The body is represented by an impedance $Z_S$. The right arm is modeled as an arm impedance $Z_{ra}$ connected to a hand resistance $R_h$. The left arm is similarly modeled, but also includes another impedance $Z_B$ inserted between the arm impedance $Z_{la}$ and hand resistance $R_h$. The impedance $Z_B$ represents the increase in brachial impedance caused by the compression of the blood-pressure cuff when it is inflated.

The blood-pressure at different locations on the living subject's body is related to the aortic pressure by the systematic impedances. For example, the blood-pressure in the right hand $P_h(t)$ and the blood-pressure in the left brachial artery $P_B(t)$ is given by:

$$P_h(t) = P_A(t)[R_h / (Z_{ra} + R_h)]; \text{ and} \tag{8}$$

$$P_B(t) = P_A(t)[(Z_{la} + R_h) / (Z_{la} + Z_B + R_h)]. \tag{9}$$

As seen in Equations (8) and (9), the blood pressure in the right hand and the blood pressure in the left brachial artery are both dependent upon the aortic pressure. Combining Equations (8) and (9), the brachial blood pressure $P_B(t)$ is given by:

$$P_B(t) = P_h(t)[(Z_{la} + R_h)(Z_{ra} + R_h)] / [R_h(Z_{la} + Z_B + R_h)]. \tag{10}$$

The difference in blood pressure between the right hand and the left brachial artery is typically a slightly lower mean blood pressure and a higher pulse pressure in the hand. The reduction in mean blood pressure in the hand is due to viscous resistance losses that occur in any type of flow through a system of tubes. The common amplification of pulse-pressure in the hands is due to distortion of the pulse-wave shape as it passes through the compliant vessels.

The distortion of the pulse-wave shape is a result of the frequency dependence of the pulse-wave velocity which is governed by the compliance of the vessel wall. The distortion of the pulse-wave shape results in different systolic (maximum) and diastolic (minimum) blood pressures at different points in the arterial tree. The positional variation in blood pressure varies from one individual to another. The positional variation in blood pressure also varies within each individual as vasomotor tone varies.

However, the beat-to-beat variation of the vasomotor tone is generally small in a living subject with stable blood pressure. This is because the autonomic nervous system controls the vasomotor tone, typically via secreted agents, e.g., norepinephrine. For a living subject with a given vasomotor state, the relationship between the blood pressure at one location to the blood pressure at another location is dependent upon the pressure and flow characteristics (impedance) between the heart and the points on the living subject where the blood-pressure measurements are taken. These relationships tend to change little from beat to beat. Thus, an assumption is made that the relationship between the blood pressure at one location to the blood pressure at another location will remain constant if the cardiac output remains constant.

If the vascular impedances and resistances remain constant, changes in aortic pressure will cause proportional changes in the finger and brachial blood pressures. Furthermore, if two sequential heartbeats produce different aortic pressures, $P_A(i)$ and $P_A(i+1)$, due to cardiac output changes in which the impedances and resistances remaining constant, the following relationship holds true:

$$P_A(i)/P_A(i+1)=P_R(i)/P_R(i+1)=P_h(i)/P_h(i+1). \quad (11)$$

Given the relationships and assumptions described above, it is possible to estimate the change in blood pressure at one location, due to a change in cardiac output from beat to beat, if the change in pressure at another location for the corresponding beat is known.

Changes that occur in the signal $SM_2$ from the photoelectric pulse-wave detector 56 is proportional to the change in blood volume in the appendage to which the photoelectric pulse-wave detector 56 is attached, preferably the finger. The signal produced due to the change in blood volume is referred to as the plethysmographic signal. As discussed above, blood vessels are compliant tubes with diameters that vary as a function of the pressure inside the blood vessel. Accordingly, the volume of the blood vessel changes as the blood pressure in the blood vessel changes. The change in blood volume measured by the photoelectric pulse-wave detector 56 corresponds to the change in the blood vessel volume produced by the pulse pressure. This relationship is expressed as:

$$P_f = C_f \Delta V_f = K_{ox} SM_2 \quad (12)$$

where:

$P_f$ is the pulse pressure in the finger;

$C_f$ is the compliance of the blood vessels in the finger;

$\Delta V_f$ is the change in volume of the finger;

$K_{ox}$ is a constant that relates the photoelectric pulse-wave detector signal to the change in finger volume; and $SM_2$ is the plethysmographic signal produced by the photoelectric pulse-wave detector 56.

As indicated above, the blood pressures in the finger and the brachial artery vary as a function of the aortic pressure. In addition, changes in the blood pressure in the finger will be proportional to changes in the brachial blood pressure if the vascular impedances do not change. Therefore, for two heartbeats having different pulse pressures $P_f(1)$ and $P_f(2)$, $$P_f(1)/P_f(2)=SM_2(1)/SM_2(2)=P_B(1)/P_B(2). \quad (13)$$

$P_B(a)$ represents the brachial pulse pressure produced by an altered stroke volume that produces an altered volumetric change in the finger $\Delta V_f(a)$. With knowledge of the volumetric change in the finger $\Delta V_f(n)$ produced by a normal pulse, the brachial pulse pressure $P_B(C)$ that would have been produced had the stroke volume been normal is estimated as:

$$\Delta V_f(a)/\Delta V_f(n)=P_B(a)/P_B(c); \text{ or} \quad (14)$$

$$P_B(c)=P_B(a)[\Delta V_f(n)/\Delta V_f(a)]. \quad (15)$$

The amplitude of an oscillometric pulse signal $SM_1$ filtered from a cuff pressure signal $P_C$ is a function of the change in brachial pulse pressure. The change in brachial pulse pressure $P_B$ produces a change in the amplitude of the oscillometric pulse signal $SM_1$, as follows:

$$SM_1=(K_D C_B/V_o)P_B \quad (16)$$

where:

$K_D$ is the deflation rate of the cuff;

$C_B$ is the compliance of the brachial artery at a cuff pressure $P_C$; and $V_o$ is the volume of the cuff.

An oscillometric pulse signal $SM_1(a)$ caused by an abnormal stroke volume is given by:

$$SM_1(a)=(K_D C_B/V_o)P_B(a). \quad (17)$$

To correct the oscillometric pulse signal $SM_1(a)$ caused by an abnormal stroke volume to a corrected oscillometric pulse signal $SM_1(c)$ with the same amplitude as an oscillometric pulse signal caused by a normal pulse, the following relationships are used:

$$SM_1(c)=(K_D C_B/V_o)P_B(c); \text{ and} \quad (18)$$

$$SM_1(c)=(K_D C_B/V_o)P_B(a)[\Delta V_f(n)/\Delta V_f(a)]. \quad (19)$$

Alternatively, an oscillometric pulse signal $SM_1(a)$ caused by an abnormal stroke volume can be corrected by substituting Equation (17) into Equation (18) as follows:

$$SM_1(c)=SM_1(a)[\Delta V_f(n)/\Delta V_f(a)]. \quad (20)$$

An oscillometric-systolic-pressure correcting circuit 116 corrects the oscillometric pressure when the living subject's blood pressure changes during the oscillometric blood-pressure measurement.

During the course of a blood-pressure measurement by the blood-pressure measuring circuit 90, the oscillometric-systolic-pressure correcting circuit 116 identifies and stores the exact pulses at which both the systolic and diastolic blood pressures are determined. In addition, the oscillometric-systolic-pressure correcting circuit 116 stores the pulse propagation time for each pulse during the blood-pressure measurement by measuring the delay time between predetermined periodic points on the electrocardiographic waveform and predetermined periodic points on the corresponding photoelectric pulse-wave waveform, as described above. The oscillometric-systolic-pressure correcting circuit 116 indexes each delay time so that it can be associated with the oscillometric pulse for the corresponding heartbeat.

After the blood-pressure measuring circuit 90 determines the living subject's systolic blood pressure during the cuff blood-pressure measurement, the oscillometric-systolic-pressure correcting circuit 116 identifies the heartbeat that occurred at the time the living subject's systolic blood pressure was determined. The oscillometric-systolic-pressure correcting circuit 116 then verifies that the heartbeat that occurred at the time that the living subject's systolic blood pressure was determined was not an arrhythmia or a motion artifact.

If the heartbeat was normal, the blood-pressure/pulse-wave-propagation-information-relationship determining circuit 94 uses the propagation time of the pulse that corresponds to the heartbeat to calibrate the equation relating the propagation time to the systolic blood pressure, as described above. If the heartbeat was an arrhythmia and arrhythmia correction was done, the blood-pressure/pulse-wave-propagation-information-relationship determining circuit 94 determines the calibration equation as if it were a normal heartbeat.

If the oscillometric pulse is identified as a motion artifact or an uncorrected arrhythmia, the blood-pressure/pulse-wave-propagation-information-relationship determining circuit 94 determines the calibration equation using the average delay time for the normal pulses that preceded the systolic blood-pressure-determination pulse.

The oscillometric-systolic-pressure correcting circuit 116 then analyzes the estimated systolic blood pressure determined by the estimated-blood-pressure determining circuit 96 over the interval between the systolic blood-pressure measurement and diastolic blood-pressure measurement by the cuff 12 to determine if a significant change in blood pressure has occurred. A significant change is defined as a progressive change in blood pressure that exceeds a multiple of an established error for the estimated systolic blood pressure. If the oscillometric pulse used to determine the systolic blood pressure was produced by an arrhythmia or a motion artifact, the threshold for determining a significant change is increased.

If the estimated systolic blood pressure did not change significantly, the systolic and diastolic blood pressures determined by the blood-pressure measuring circuit 90 are displayed. If the estimated systolic blood pressure changes significantly over the systolic-diastolic blood-pressure measurement interval, the estimated systolic blood pressure for the pulse from which the diastolic blood pressure was determined by the blood-pressure measuring circuit 90 is displayed.

A quality-assurance and data-checking circuit 118 performs quality checks on the blood-pressure measurement data to verify that there are no other causes for the apparent change in the estimated systolic blood pressure during the blood-pressure measurement. Possible causes for an apparent change in the systolic blood pressure include an excessive number of arryhthmias or motion artifacts, an excessively high cuff deflation rate, error signals from the photoelectric pulse-wave detector 56, e.g., a "no-measurement" condition from the photoelectric pulse-wave detector 56, a high uncertainty in the estimated systolic blood-pressure computation, very low mean blood pressure, etc.

The quality-assurance and data-checking circuit 118 utilizes quality-assurance rules and criteria 120 stored in the ROM 36. If the quality-assurance and data-checking circuit 118 determines that the quality of the data is not adequate, it initiates another blood-pressure measurement by the blood-pressure measuring circuit 90 and informs a caregiver of the cause for the repeated measurement.

Predetermined logic statements, i.e., questions, for performing user-specified living subject evaluation checks 122 are stored in the ROM 36. The user-specified evaluation checks will be described in more detail.

The oscillometric-systolic-pressure correcting circuit 116 preferably displays the estimated systolic blood pressure in a manner that identifies it as an estimated value. The estimated systolic blood-pressure value is preferably displayed separately from the oscillometric systolic blood-pressure value measured with the inflatable cuff 12. Alternatively, the estimated systolic blood-pressure value can be displayed in place of the actual measured systolic blood-pressure value by having the estimated systolic blood-pressure value displayed as a flashing value, or displayed with an asterisk beside the value.

In addition, the oscillometric-systolic-pressure correcting circuit 116 preferably also displays the reason for displaying the estimated systolic blood-pressure value, e.g., the caregiver is informed that the living subject's blood pressure was falling or rising during the blood-pressure measurement. Other information, e.g., the presence of arrhythmias, changes in the heart rate, and the ejection fraction determined from the photoelectric pulse-wave pulse, can also be displayed.

Figure 9A:
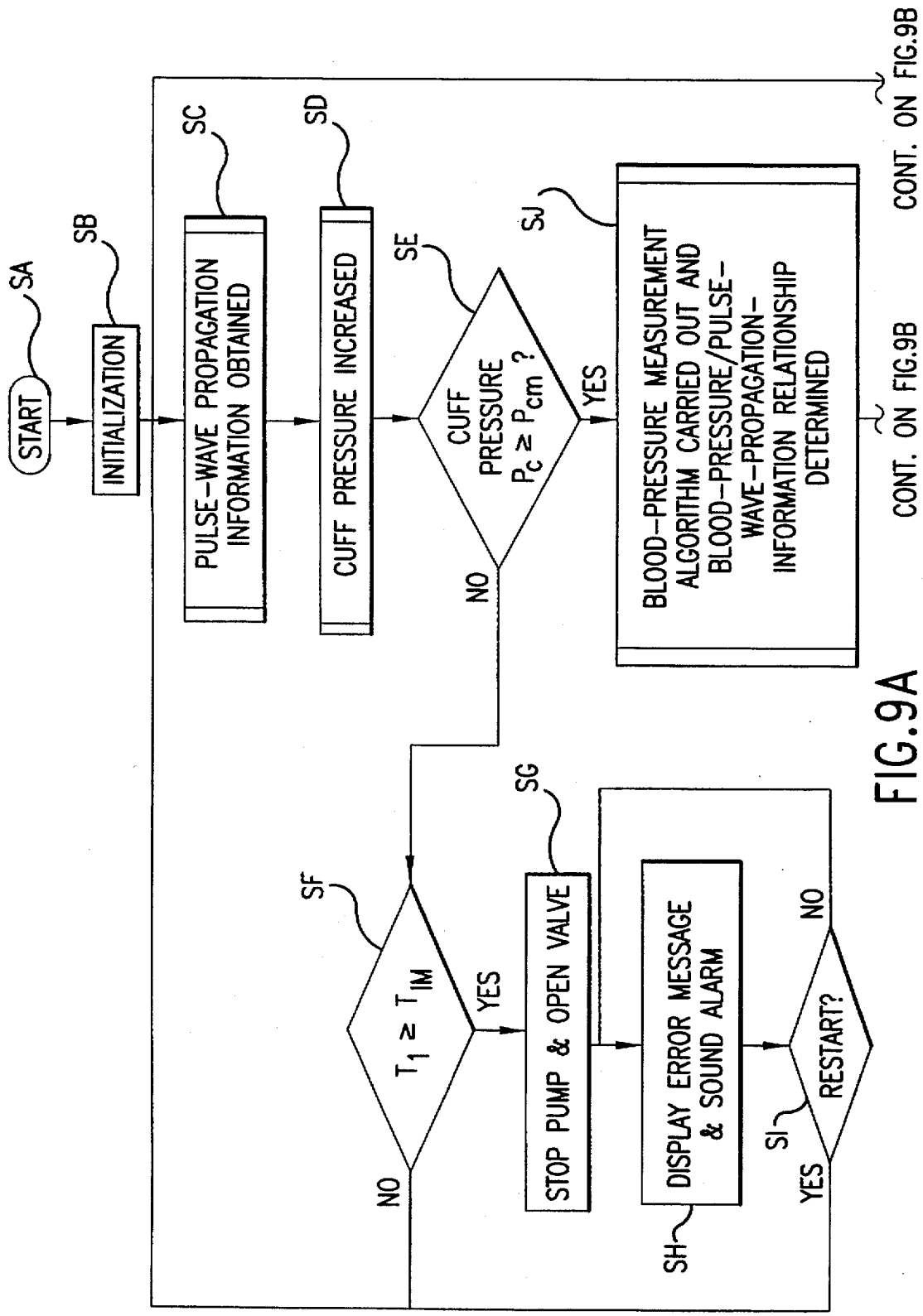
FIGS. 9A–9B show a flowchart of a preferred control routine for the blood-pressure measurement system of FIGS. 2 and 4.
Figure 9B:
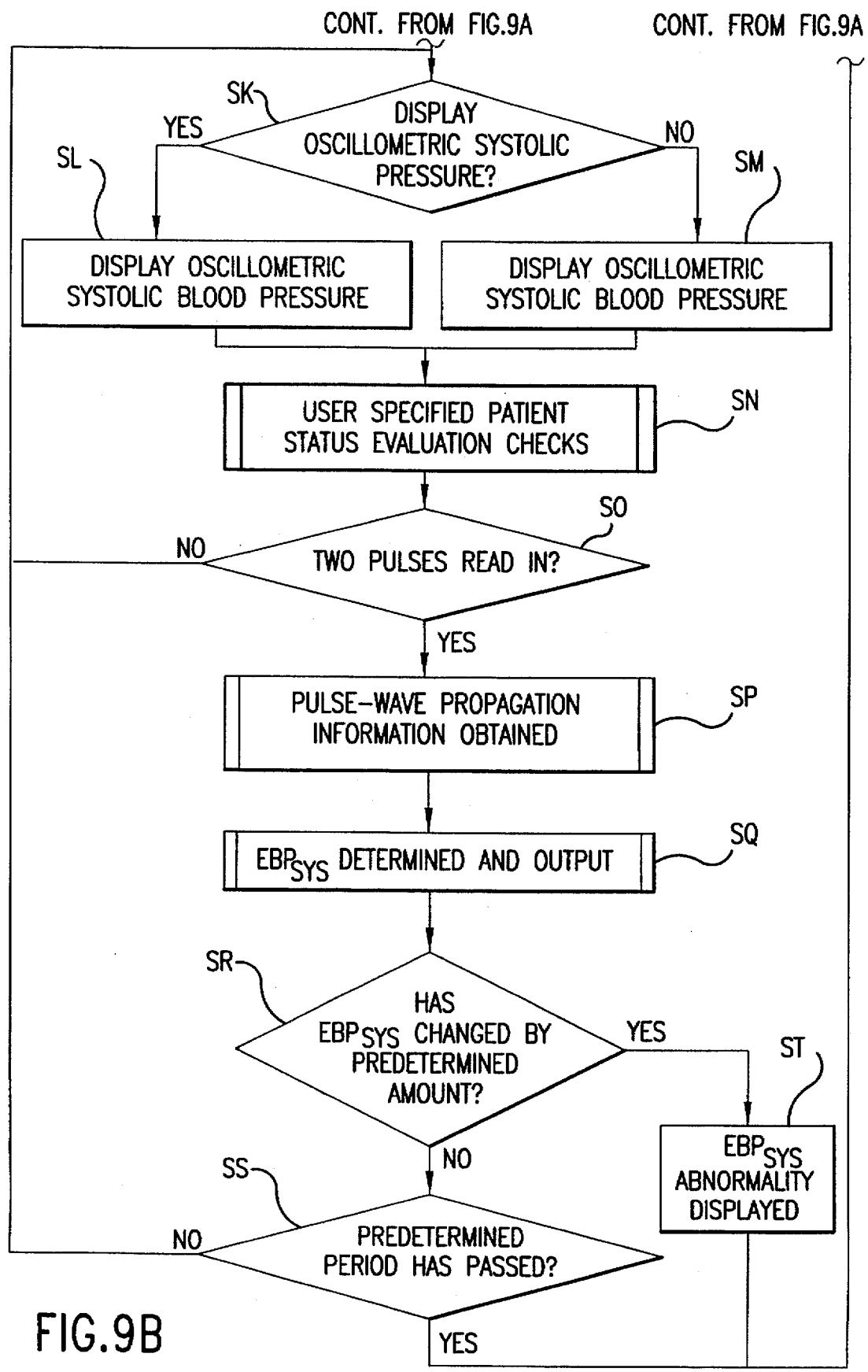
Figure 9B:
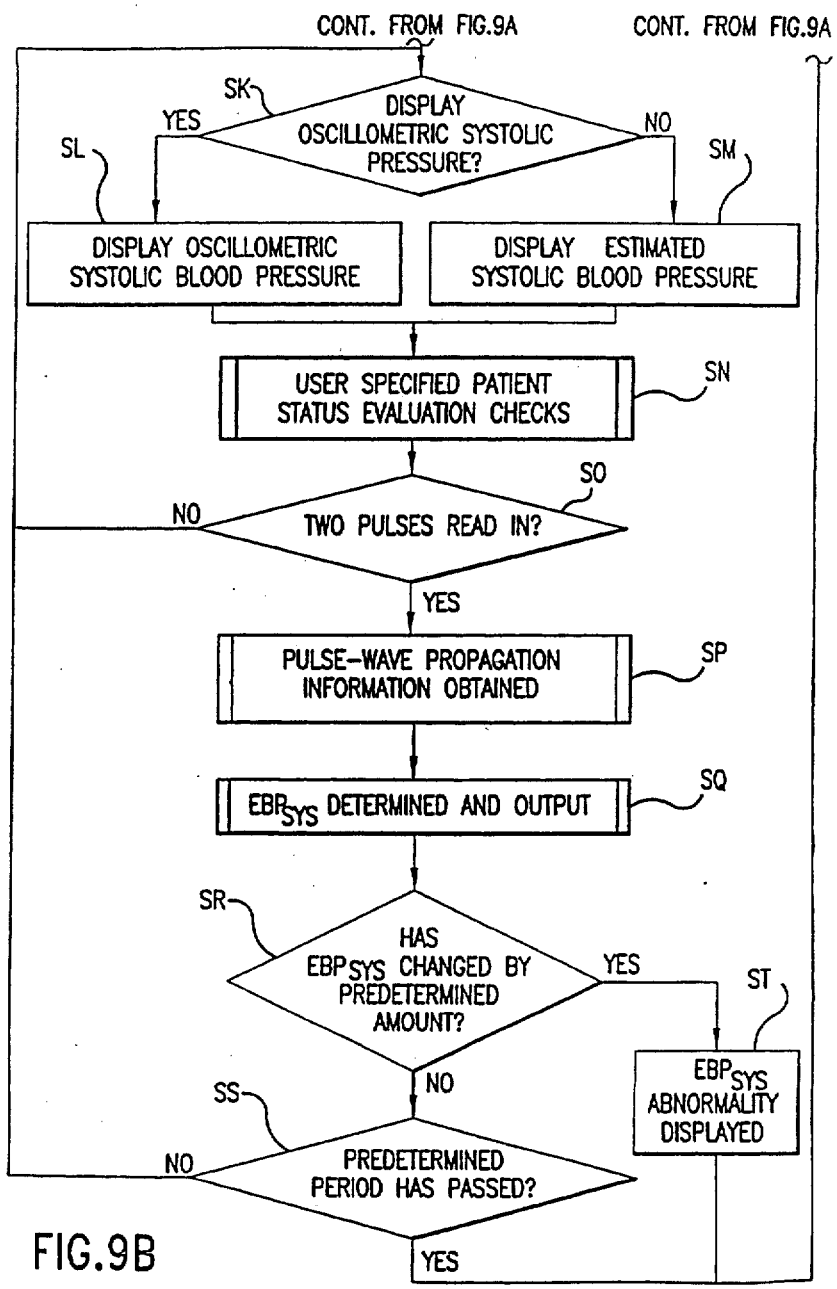
Figure 12A:
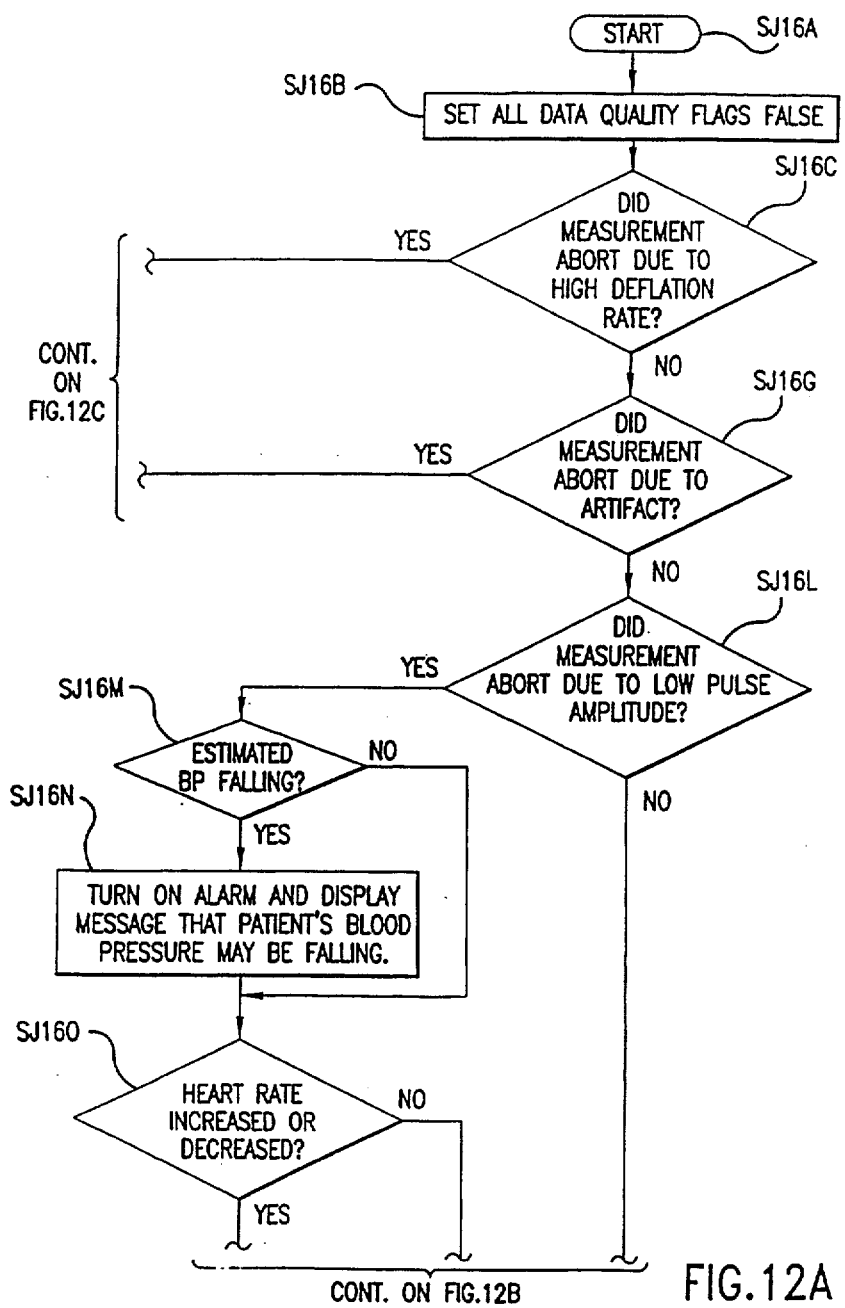
Figure 12B:
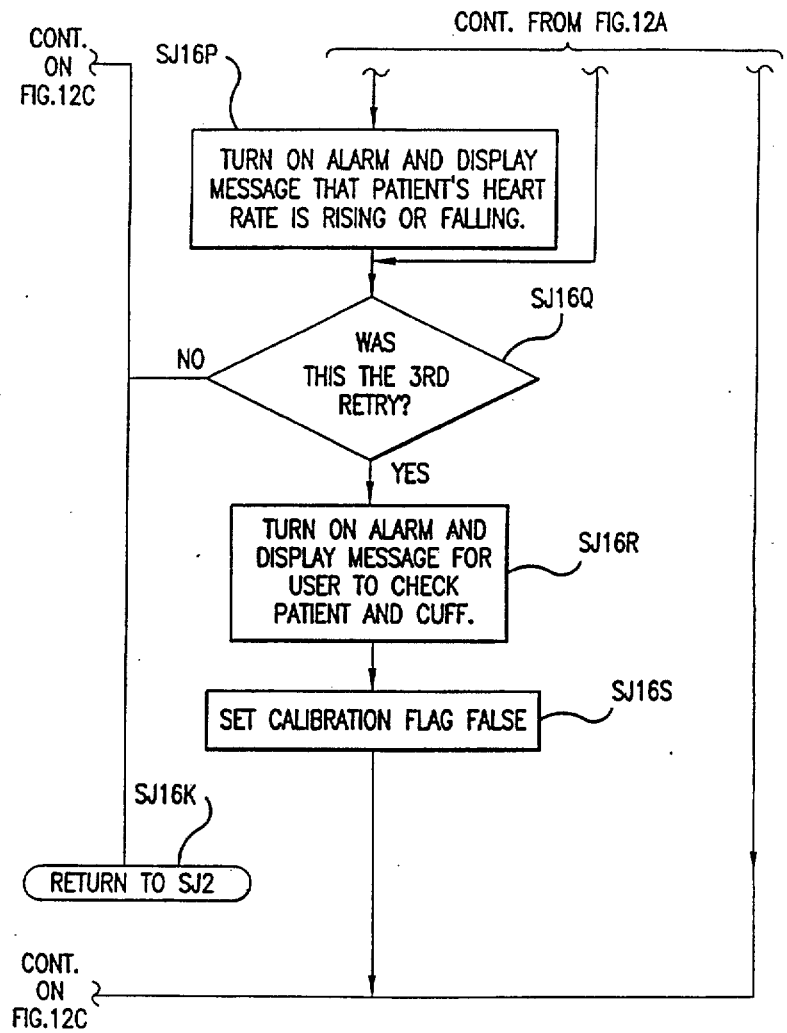
Figure 12C:
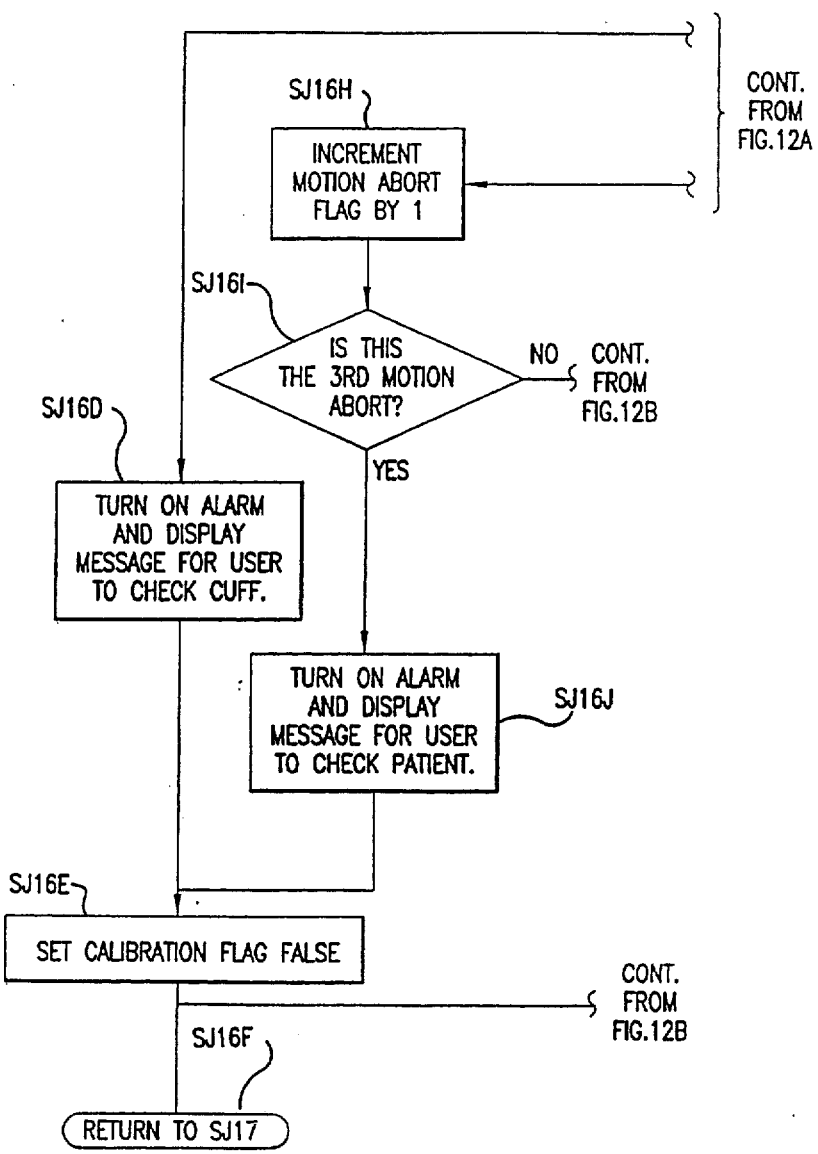
Figure 13A:
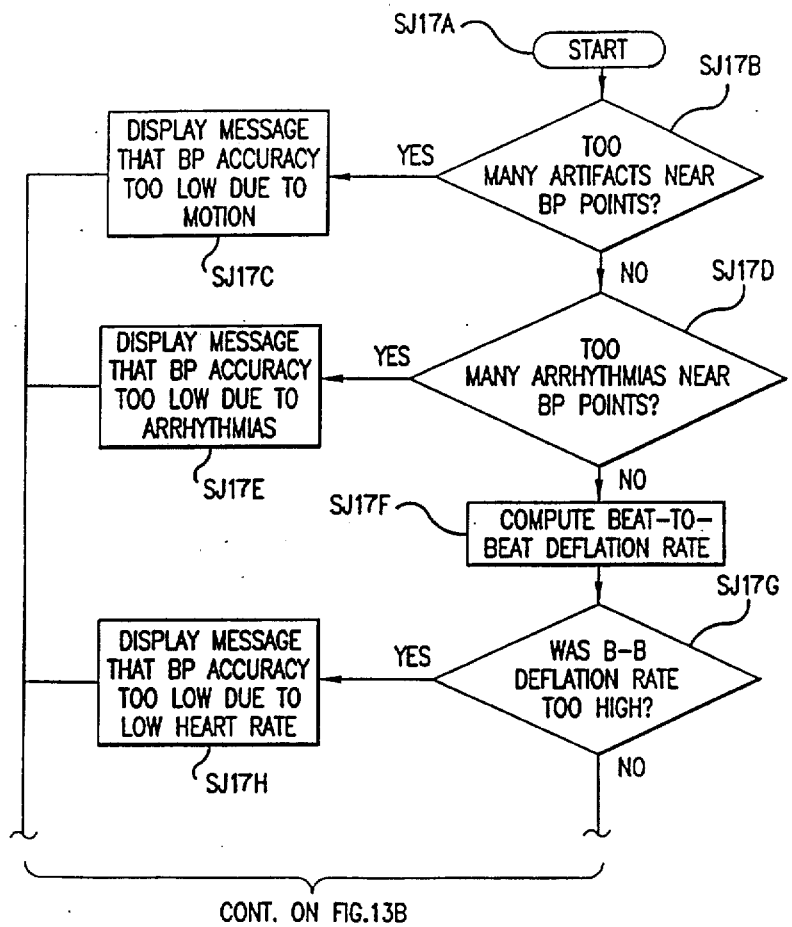
Figure 13B:
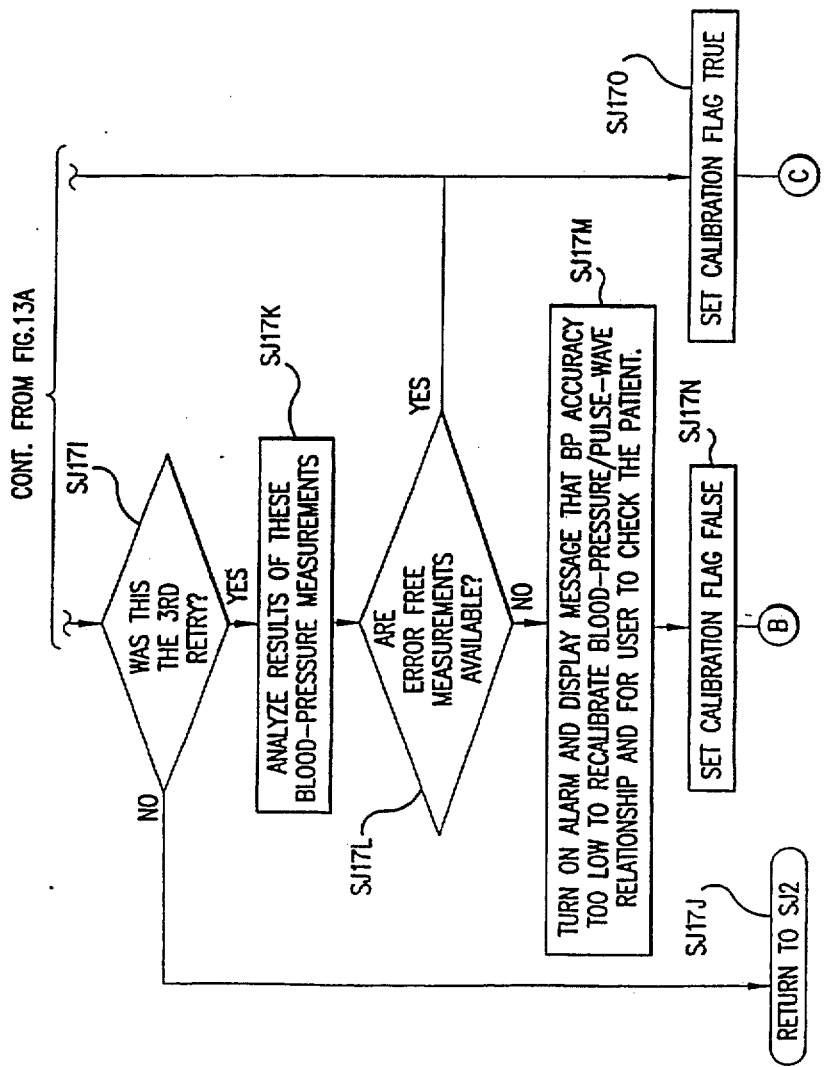
Figure 13C:
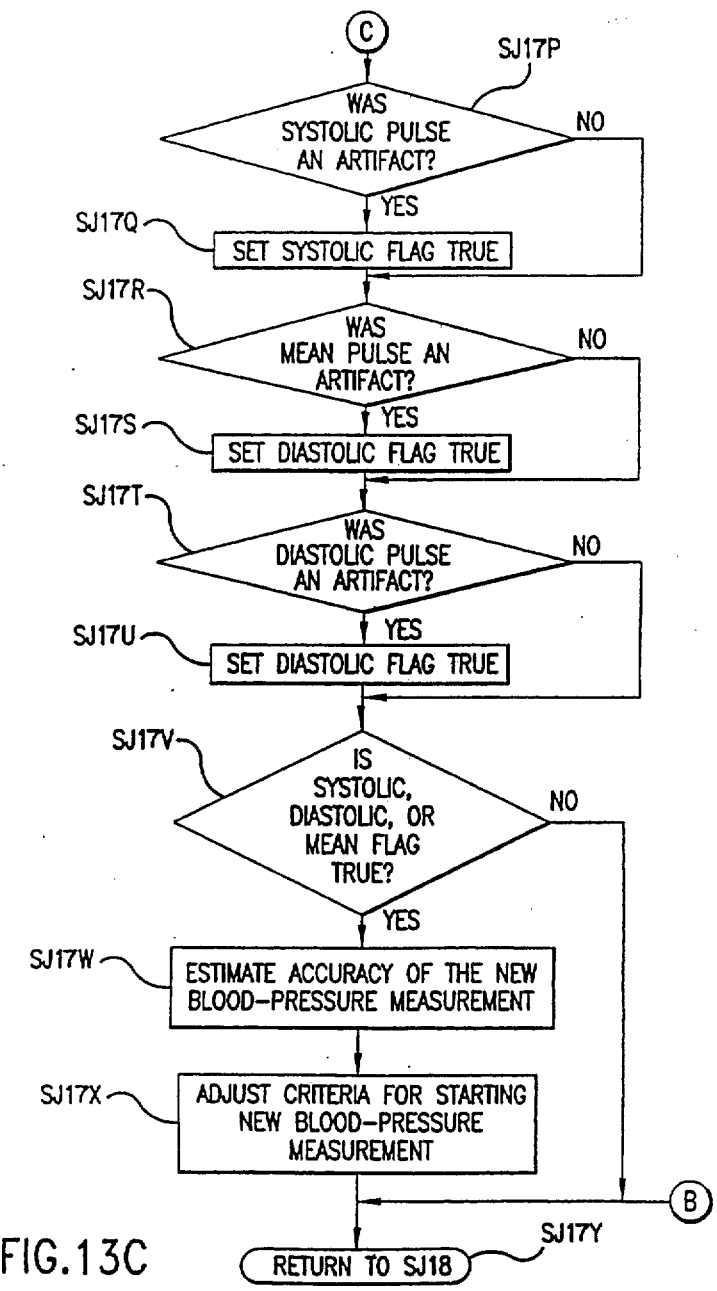
Figure 14:
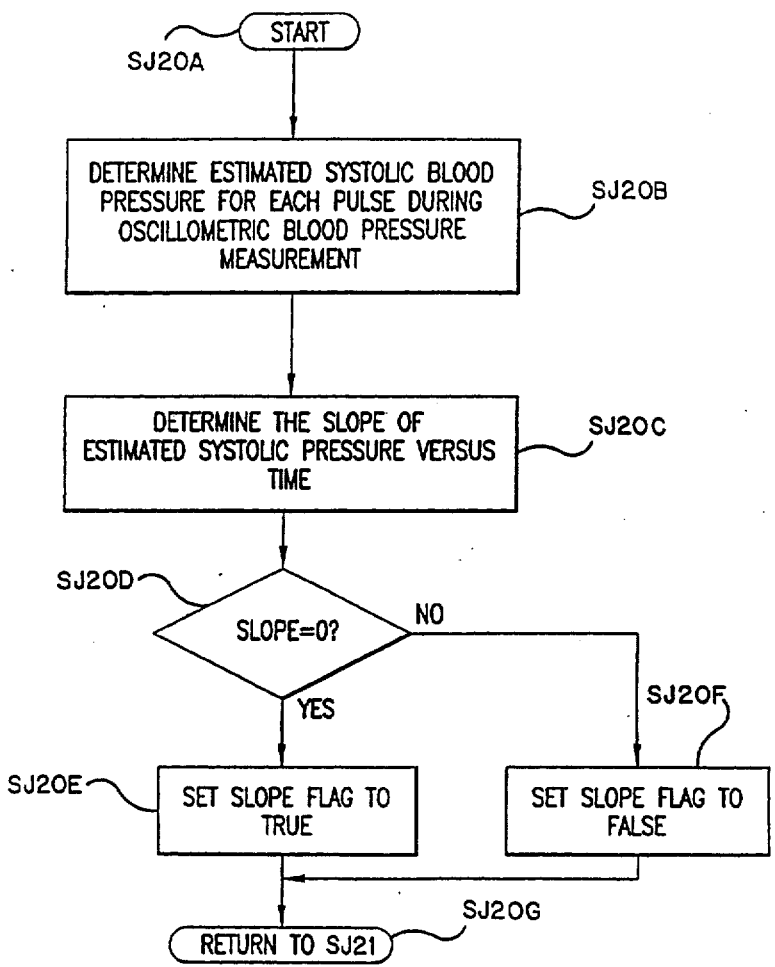

FIG. 9 shows a preferred control routine for the blood-pressure measurement system 10 of this invention. The routine starts as step SA and proceeds to step SB, where flags, counters and registers (not shown) are reset.

Next, at step SC, the control system determines a pulse-wave propagation time $DT_{RP}$ and determines a pulse-wave propagation velocity $V_M$ based on the determined pulse-wave propagation time $DT_{RP}$. Control then continues to step SD, where the control system increases the air pressure in the inflatable cuff 12 by switching the selector valve 20 to the inflation position and turning on the air pump 22.

At step SE, the control system determines if the air pressure $P_C$ in the inflatable cuff 12 has reached a predetermined maximum cuff pressure $P_{CM}$. If the cuff pressure $P_C$ is less than $P_{CM}$, control continues to step SF. Otherwise, control jumps to step SJ.

At step SF, the control system determines whether the elapsed time since the start of the cuff inflation $T_I$ has reached a predetermined maximum inflation time $T_{IM}$. If $T_I$ is greater than or equal to $T_{IM}$, control continues to step SG. Otherwise, control returns to step SC.

At step SG, the control system turns off the air pump 22 and switches the selector valve 20 to an open position, i.e., the quick-deflation position. Next, at step SH, the control system displays an error message on the display device 44 notifying the user that the inflatable cuff 12 cannot be inflated. The control system also sounds an alarm. Control then continues to step SI.

At step SI, the control system goes into a standby mode and waits until a restart is initiated by the user. If a restart is initiated by the user, control returns to step SC. Otherwise, control returns to step SH.

At step SJ, the control systems switches the selector valve 20 to the slow-deflation position. In addition, the control system initiates a blood-pressure measuring algorithm and determines a blood-pressure/pulse-wave-propagation-information relationship using the preferred control routine shown in FIGS. 9A and 9B.

The control system then begins a continuous monitoring of the living subject's blood pressure using an estimated blood pressure determined on a beat-by-beat basis utilizing the blood-pressure/pulse-wave-propagation-information relationship.

The continuous monitoring process begins at step SK, where the control system determines if a user has requested a change in the type of systolic blood pressure that is displayed by the control system for the last oscillometric blood-pressure measurement. A user requests a change in the systolic blood pressure displayed by entering instructions through the user input device 46. If a user requests the display of oscillometric systolic blood pressure, control continues to step SL, where the control system displays the actual oscillometric systolic blood pressure determined in the previous oscillometric blood-pressure measurement. Otherwise, control jumps to step SM, where the control system displays the systolic blood pressure estimated using the blood-pressure/pulse-wave-propagation-information relationship. From either step SL or step SM, control continues to step SN.

Figure 16:
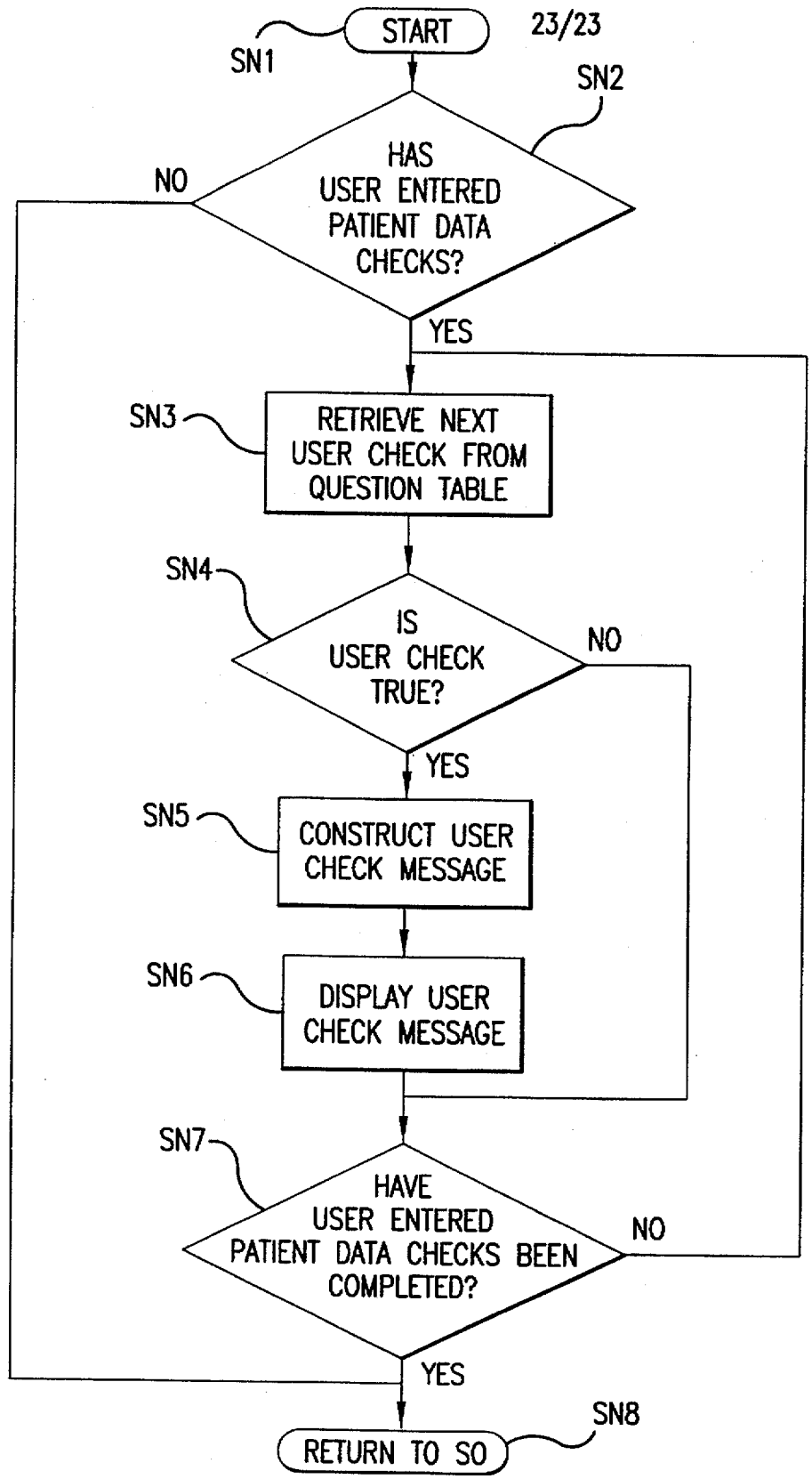
FIG. 16 shows a flowchart of a preferred control subroutine for performing user-specified, living subject status evaluation checks.
Figure 1:
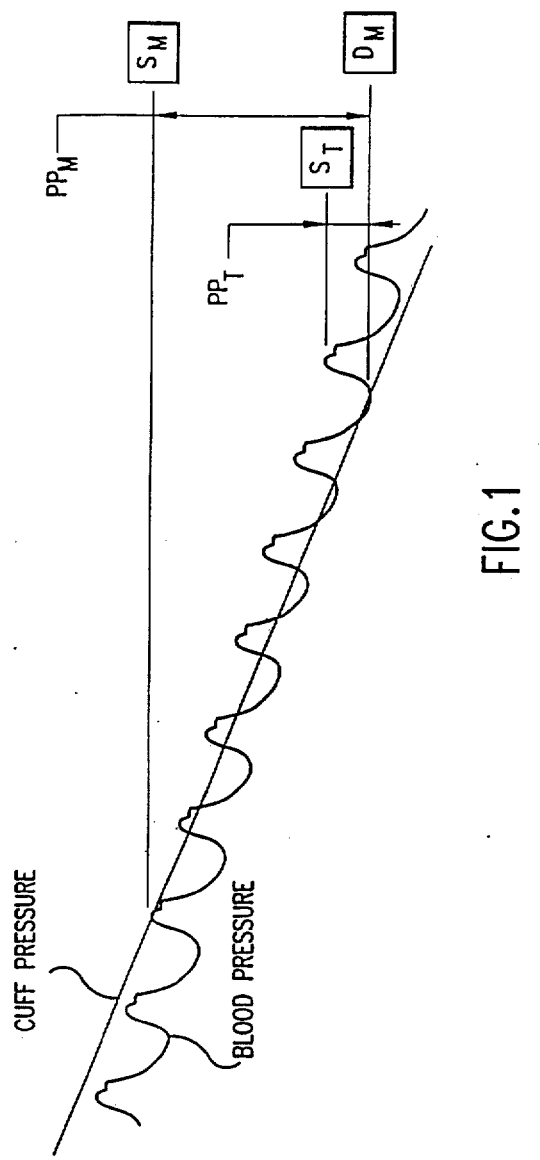
Figure 2:
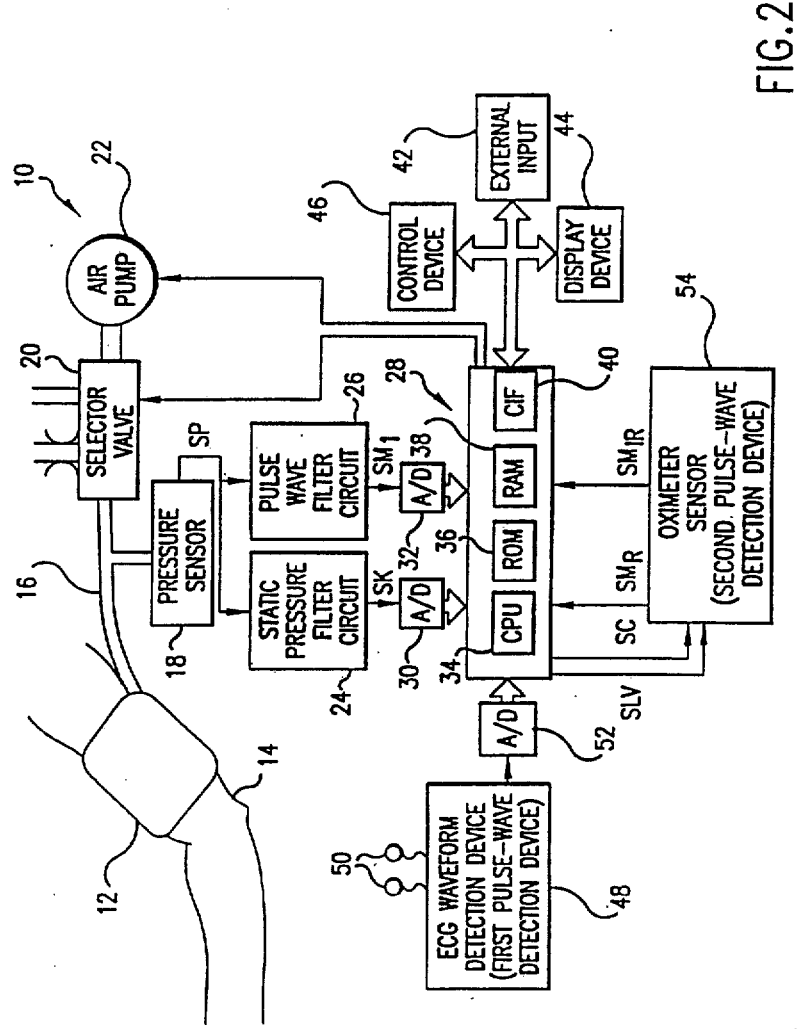
Figure 5A:
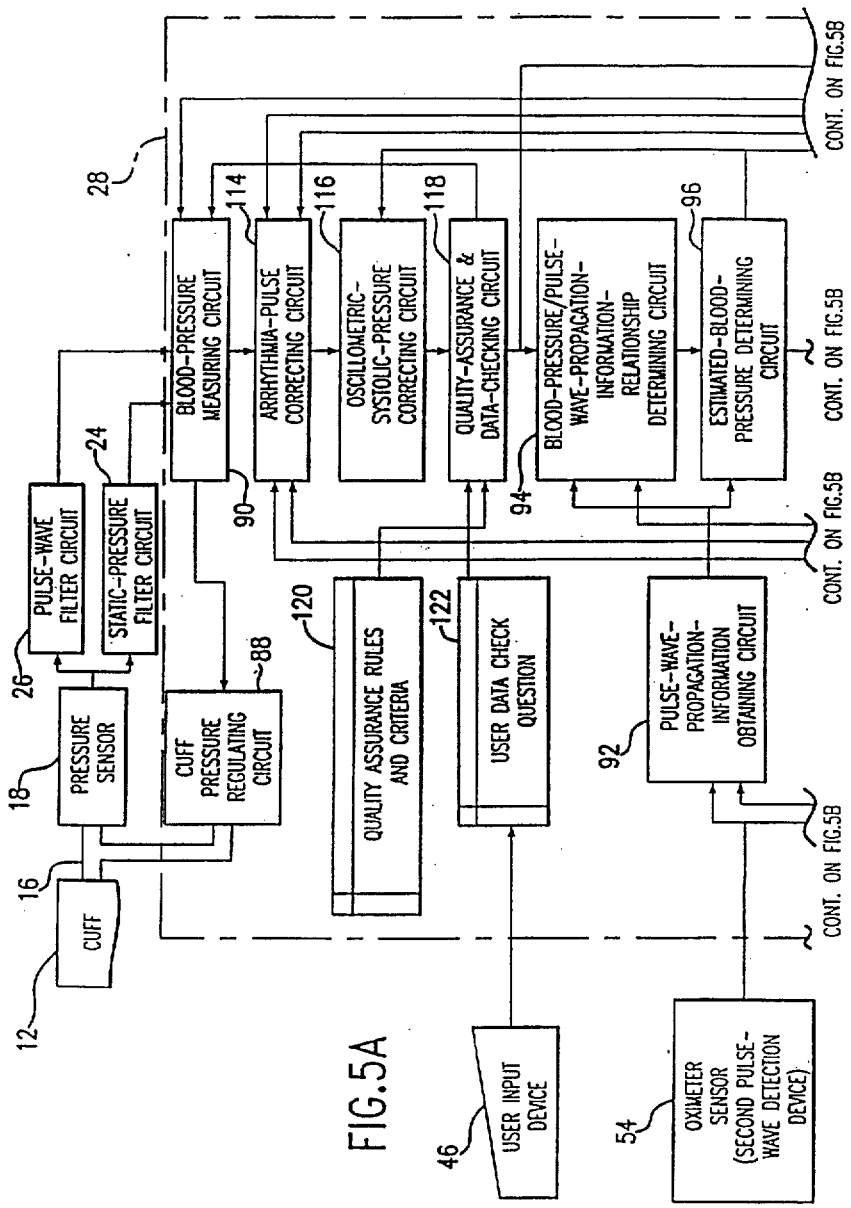
Figure 5B:
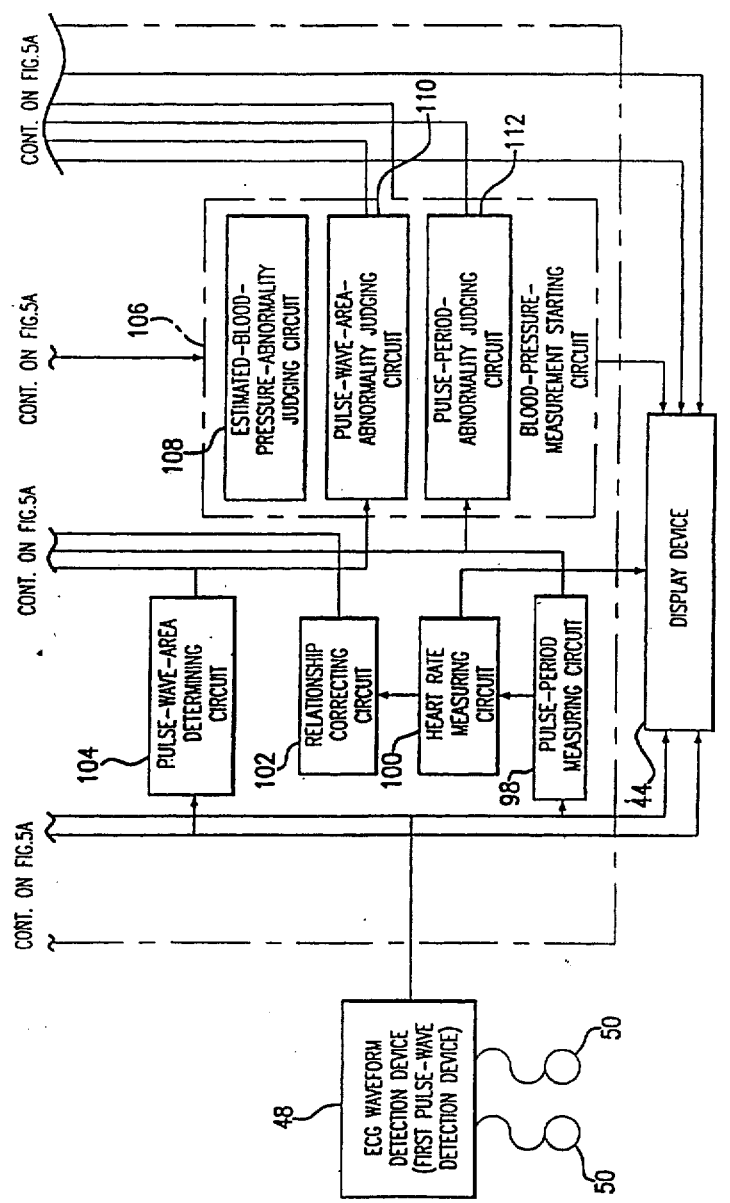
Figure 8:
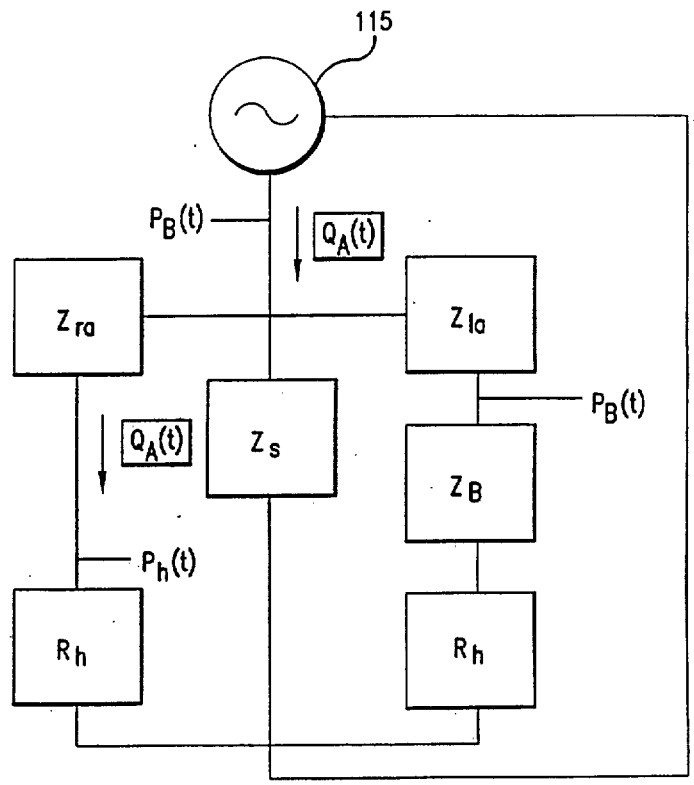

At step SN, the control system performs individualized, user-specified patient status evaluation checks using the preferred control routine shown in FIG. 16. Control then continues to step SO.

At step SO, the control system determines if two plethysmographic pulses detected by the photoelectric pulse-wave detector 56 have been captured. If so, control continues to step SP. Otherwise, control returns to step SK.

At step SP, the control system determines the pulse-wave propagation time $DT_{RP}$ and the pulse-wave propagation velocity $V_M$. Control then continues to step SQ, where the control system determines and displays the estimated systolic blood pressure $EBP_{SYS}$. The control system determines the estimated systolic blood pressure $EBP_{SYS}$ using the blood-pressure/pulse-wave-velocity relationship determined at step SJ and the pulse-wave velocity VM determined at step SP. Control then continues to step SP.

At step SR, the control system compares the latest estimated systolic blood pressure to the previously estimated systolic blood pressures and determines if the estimated systolic blood pressure has changed by a predetermined amount. If the estimated systolic blood pressure has not changed by a predetermined amount, control continues to step SS. Otherwise, control jumps to step ST.

At step SS, the control system determines if a predetermined time for starting a new oscillometric blood-pressure measurement has elapsed. The predetermined time between oscillometric blood-pressure measurements is preferably set by a user via the user input device 46. If the predetermined time period has elapsed, control returns to step SC, and a new oscillometric blood-pressure measurement is initiated. Otherwise, control returns to step SK.

At step ST, the control system displays a message to the user explaining the change in the estimated systolic blood pressure. The control system can also display other information which may be of use to the user in evaluating the living subject's condition, e.g., changes in the heart rate. Control then returns to step SC, where a new oscillometric blood-pressure measurement is initiated.

Figure 10A:
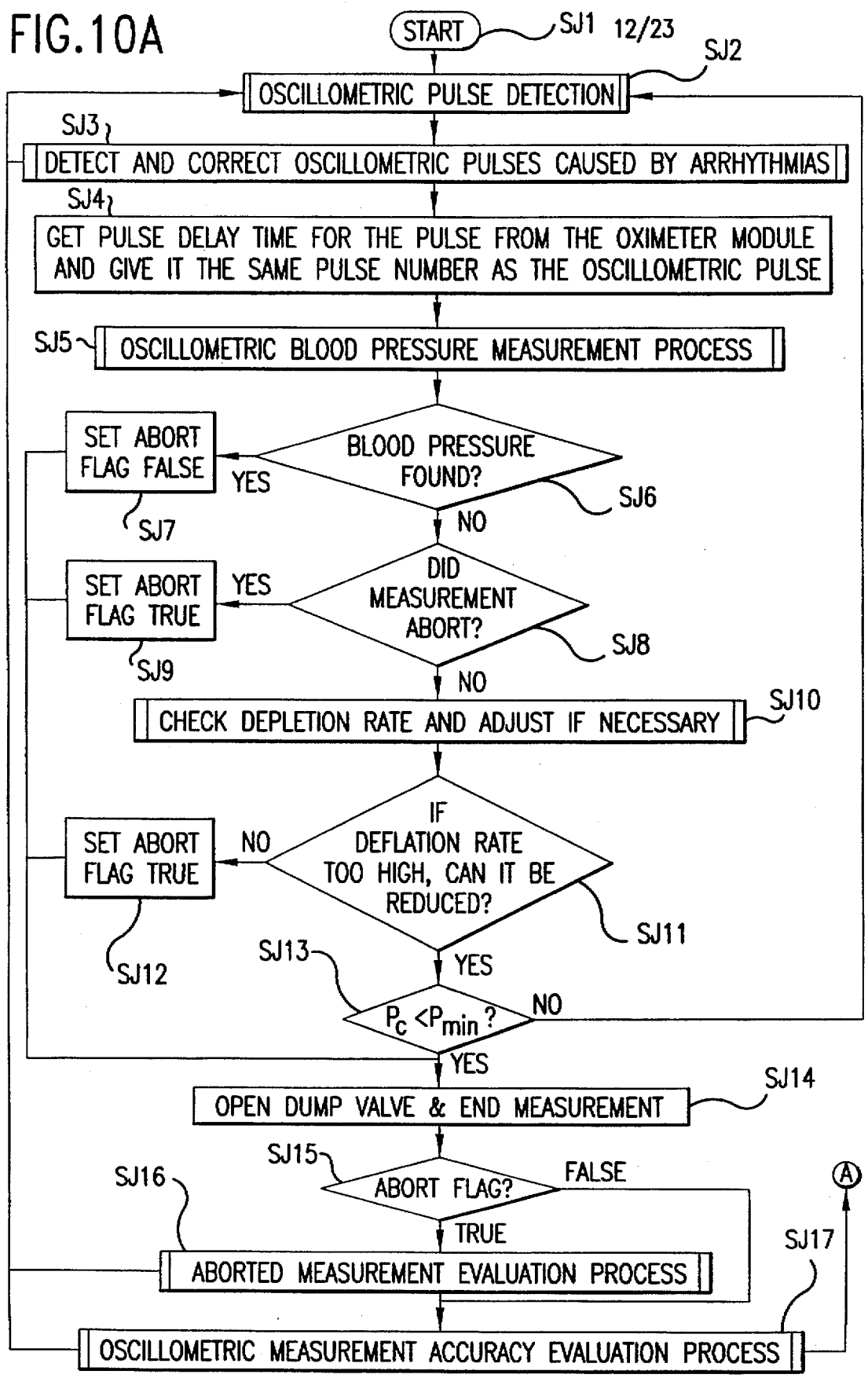

FIGS. 10A and 10B show a preferred control routine for measuring the living subject's blood pressure at step SJ. The routine starts at step SJ1 and proceeds to step SJ2, where the control system searches for an oscillometric pulse in the signal produced by the pulse-wave filter circuit 26. When the control system detects an oscillometric pulse, the amplitude of the oscillometric pulse is measured. In addition, the control system determines the air pressure in the inflatable cuff 12 at the time that the oscillometric pulse is detected. The control system determines the air pressure in the inflatable cuff 12 from the output of the static-pressure filter circuit 24. The control system assigns an index number to the amplitude of the oscillometric pulse and to the cuff pressure, and retains these values for later use. Control then continues to step SJ3.

Figure 11:
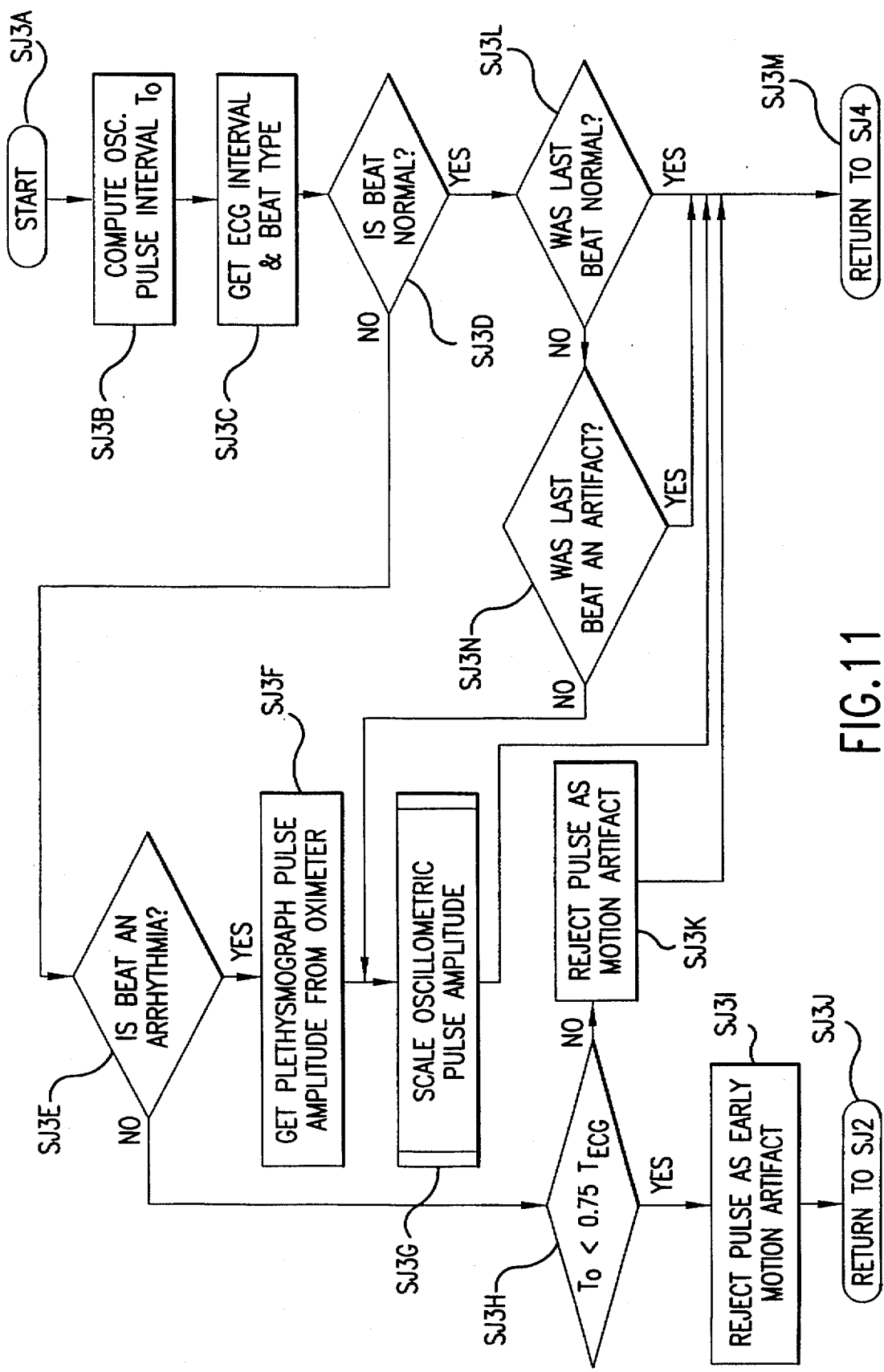
FIG. 11 shows a flowchart of a preferred control subroutine for detecting and correcting oscillometric pulses produced by arrhythmias.

At step SJ3, the control system, using the preferred control routine shown in FIG. 11, detects an oscillometric pulse and corrects the amplitude of the pulse if the pulse is produced by an arrhythmia.

Next, at step SJ4, the control system determines the pulse-wave propagation time $DT_{RP}$ for the pulse detected at step SJ3. In addition, the same index number assigned to the oscillometric pulse and its corresponding cuff pressure at step SJ2 is assigned to the pulse-wave propagation time $DT_{RP}$.

At step SJ5, the control system processes the oscillometric pulse amplitude and cuff pressure data using well-known oscillometric blood-pressure measuring techniques. Control then continues to step SJ6, where the control system determines if the living subject's systolic blood pressure, diastolic blood pressure, mean blood pressure, and oscillometric heart rate have been determined. If so, control continues to step SJ7. Otherwise, control jumps to step SJ8. At step SJ7, the control system sets an Abort Flag to "FALSE." Control then jumps to step SJ14.

At step SJ8, the control system determines if the oscillometric blood-pressure measurement was aborted. If the measurement was aborted, control continues to step SJ9. Otherwise, control jumps to step SJ10. At step SJ9, the control system sets the Abort Flag to "TRUE." Control then jumps to step SJ14.

At step SJ10, the control system checks the deflation rate of the inflatable cuff 12 and adjusts the deflation rate if it is too high or too low. Next, at step SJ11, the control system determines if the deflation rate of the inflatable cuff 12 is too high and cannot be further reduced. If an excessively high deflation rate cannot be reduced, control continues to step SJ12. Otherwise, control jumps to step SJ13.

At step SJ12, the control system sets the Abort Flag to "TRUE." Control then jumps to step SJ14.

At step SJ13, the control system determines if the pressure in the inflatable cuff $P_C$ is less than a predetermined minimum pressure value $P_{min}$. If $P_C$ is less than $P_{min}$, control continues to step SJ14. Otherwise, control returns to step SJ2 and the oscillometric pulse detection process continues.

At step SJ14, the control system switches the selector valve to the quick-deflation position and it terminates the oscillometric blood-pressure measurement. Next, at step SJ15, the control system evaluates the state of the Abort Flag. If the Abort Flag is set to "TRUE", control continues to step SJ16. Otherwise, control jumps to step SJ17.

At step SJ16, the control system performs an evaluation process, using the preferred control routine shown in FIG. 12, for determining the cause of an aborted measurement. Next, at step SJ17, the control system performs an evaluation process, using the preferred control routine shown in FIGS. 13A and 13B, to determine the accuracy of the oscillometric blood-pressure measurement. Control then continues to step SJ18.

At step SJ18, the control system determines if a reliable oscillometric blood-pressure measurement was obtained based on the "accuracy evaluation" process of step SJ17. If a reliable oscillometric blood-pressure measurement was obtained, control continues to step SJ19. Otherwise, control jumps to SJ23.

At step SJ19, the control system uses the measured oscillometric blood-pressure value to calibrate the blood-pressure/pulse-wave-velocity relationship. Control then continues to step SJ20, where the control system evaluates the stability of the living subject's blood pressure during the oscillometric blood-pressure measurement using the preferred control routine shown in FIG. 14.

Next, at step SJ21, the control system determines if the estimated blood pressure remained constant during the oscillometric blood-pressure measurement by evaluating the Slope Flag set at step SJ20. If the estimated blood pressure did not remain constant, control jumps to step SJ22. Otherwise, control continues to step SJ26, where the control system returns to step SK of the main control routine.

Figure 15:
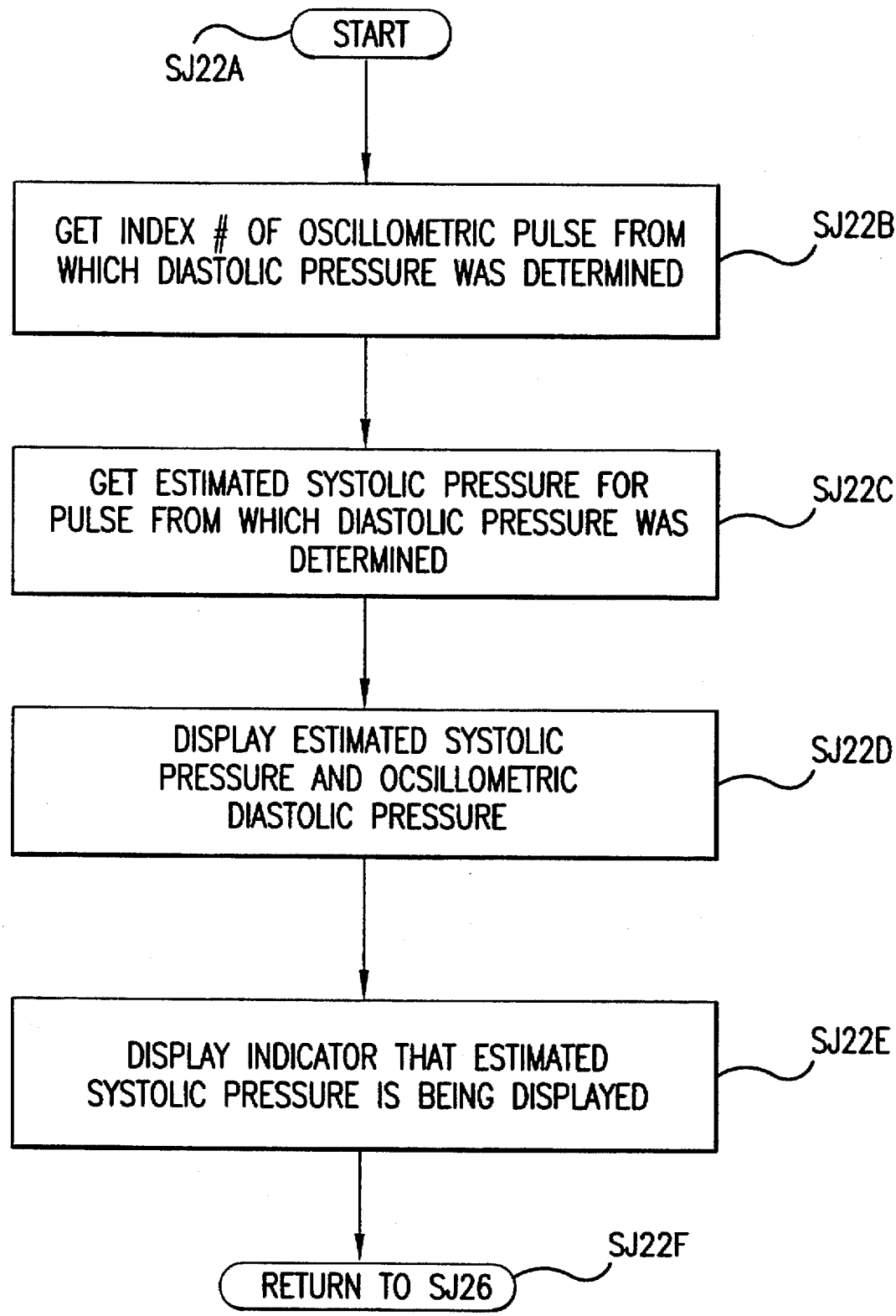
FIG. 15 shows a flowchart of a preferred control subroutine for estimating a living subject's systolic blood pressure at the end of an oscillometric blood-pressure measurement.

At step SJ22, the control system, using the preferred control routine shown in FIG. 15, estimates the systolic blood pressure of the pulse for which the oscillometric diastolic blood pressure was obtained. Control then continues to step SJ26.

At step SJ23, the control system determines if a previous blood-pressure/pulse-wave-velocity relationship is available. If a previous relationship is available, control continues to step SJ24. Otherwise, control jumps to step SJ25.

At step SJ24, the control system retains the previous blood-pressure/pulse-wave-velocity relationship for use in monitoring the living subject's blood pressure. Control then continues to step SJ26.

At step SJ25, the control system monitors the pulse-wave velocity to indirectly monitor the living subject's blood pressure, since the pulse-wave velocity changes as the subject's blood pressure changes. Control then continues to step SJ26.

FIG. 11 shows the method of detecting and correcting oscillometric pulses produced by arrhythmias of step SJ3. The control routine starts at step SJ3A and continues to step SJ3B, where the control system determines the time interval since the last detected oscillometric pulse.

Next, at step SJ3C, the control system obtains the interbeat interval between the last two electrocardiographic waveform pulses from the pulse-period measuring circuit 98. In addition, the control system obtains information on the type of pulse, i.e., normal or abnormal, for the last pulse from the pulse-wave-area-abnormality judging circuit 108. Control then continues to step SJ3D, where the control system compares the data obtained at step SJ3C with predetermined criteria to determine if the latest heartbeat is a normal beat or an arrhythmia. If the control system determines that the latest heartbeat is abnormal, control continues to step SJ3E. Otherwise, control jumps to step SJ3L.

At step SJ3E, the control system, using well-known techniques, determines if the abnormal pulse is an arrhythmic pulse or an artifact pulse based on the corresponding electrocardiographic waveform. If the control system determines that the abnormal pulse is an arrhythmic pulse, control continues to step SJ3F. Otherwise, control jumps to step SJ3H.

At step SJ3F, the control system obtains the amplitude of the last normal pulse and the amplitude of the current plethysmographic pulse from the pulse-wave waveform detected by the photoelectric pulse-wave detector 56. Next, at step SJ3G, the control system corrects the amplitude of the current oscillometric pulse using the relationship:

$$SM_1(c) = SM_1(a)[\Delta V_f(n)/\Delta V_f(a)] \quad (21)$$

where:

$SM_1(c)$ is the corrected oscillometric pulse amplitude signal;

$SM_1(a)$ is the measured oscillometric pulse amplitude signal;

$\Delta V_f(n)$ is the amplitude of the previous normal plethysmographic pulse; and $\Delta V_f(a)$ is the amplitude of the current plethysmographic pulse.

Control then continues to step SJ3M, where the control system returns to step SJ4.

At step SJ3H, the control system compares the time interval between the last oscillometric pulse and the artifact to the current electrocardiographic waveform pulse interval. If the time interval between the last oscillometric pulse and the artifact is less than 75 percent of the current electrocardiographic waveform pulse interval, control continues to step SJ3I. Otherwise, control jumps to step SJ3K.

At step SJ3I, the control system rejects the pulse as an "early motion artifact." Control then continues to step SJ3J, where the control system returns to step SJ2.

At step SJ3K, the control system rejects the pulse as a "motion artifact." Control then continues to step SJ3M.

At step SJ3L, the control system determines if the previous heartbeat was a normal heartbeat. If the last heartbeat was normal, control continues to step SJ3M. Otherwise, control jumps to step SJ3N.

At step SJ3N, the control system determines whether the previous heartbeat was an artifact or an arrhythmia. If the previous heartbeat was an artifact, the new oscillometric pulse is retained and control jumps to step SJ3M. Otherwise, the control system determines that the previous pulse was an arrhythmia, and control jumps to step SJ3G.

Figure 12A:
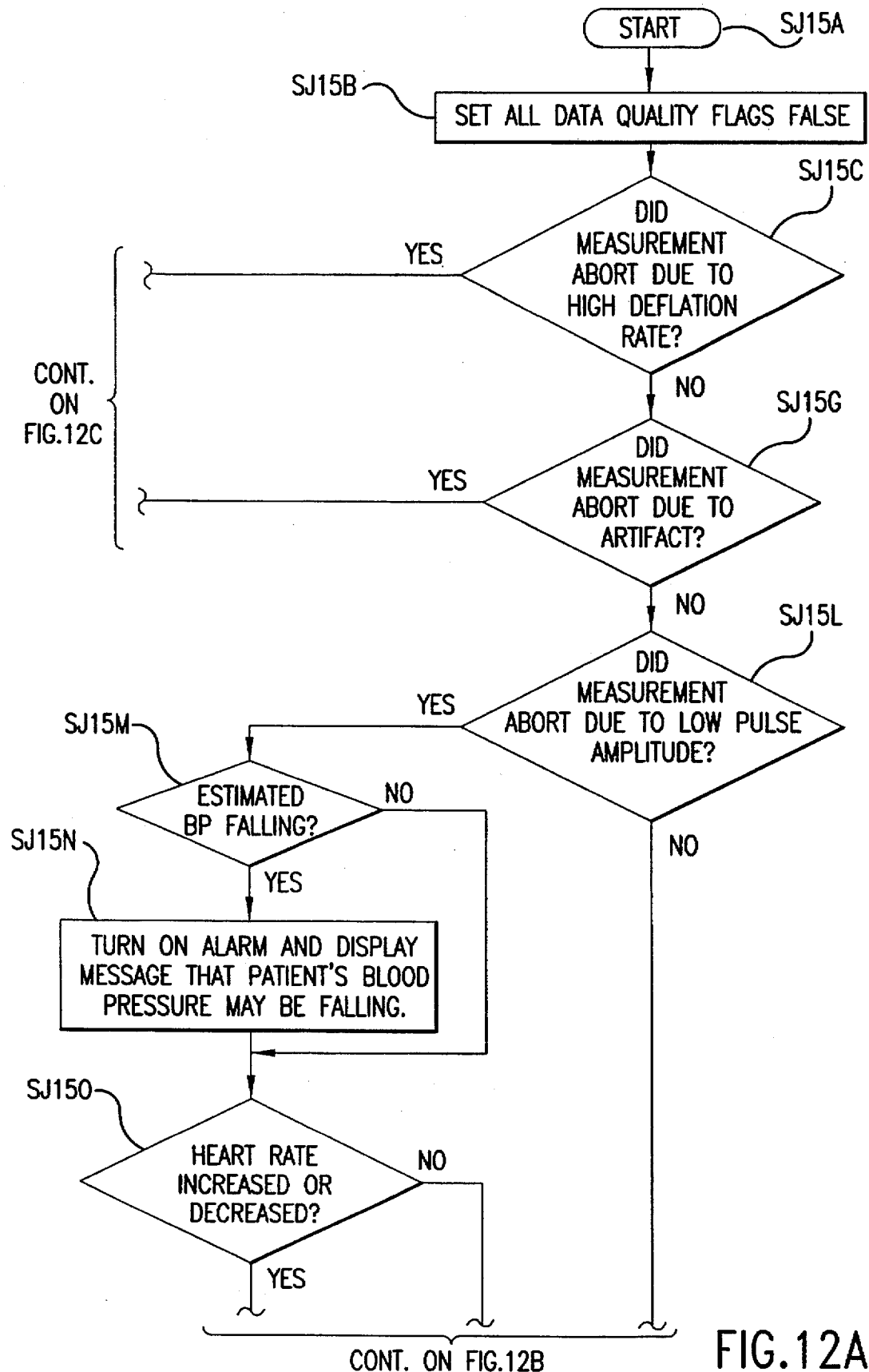
FIGS. 12A–12C show a flowchart of a preferred control subroutine for evaluating an aborted oscillometric blood-pressure measurement.
Figure 12B:
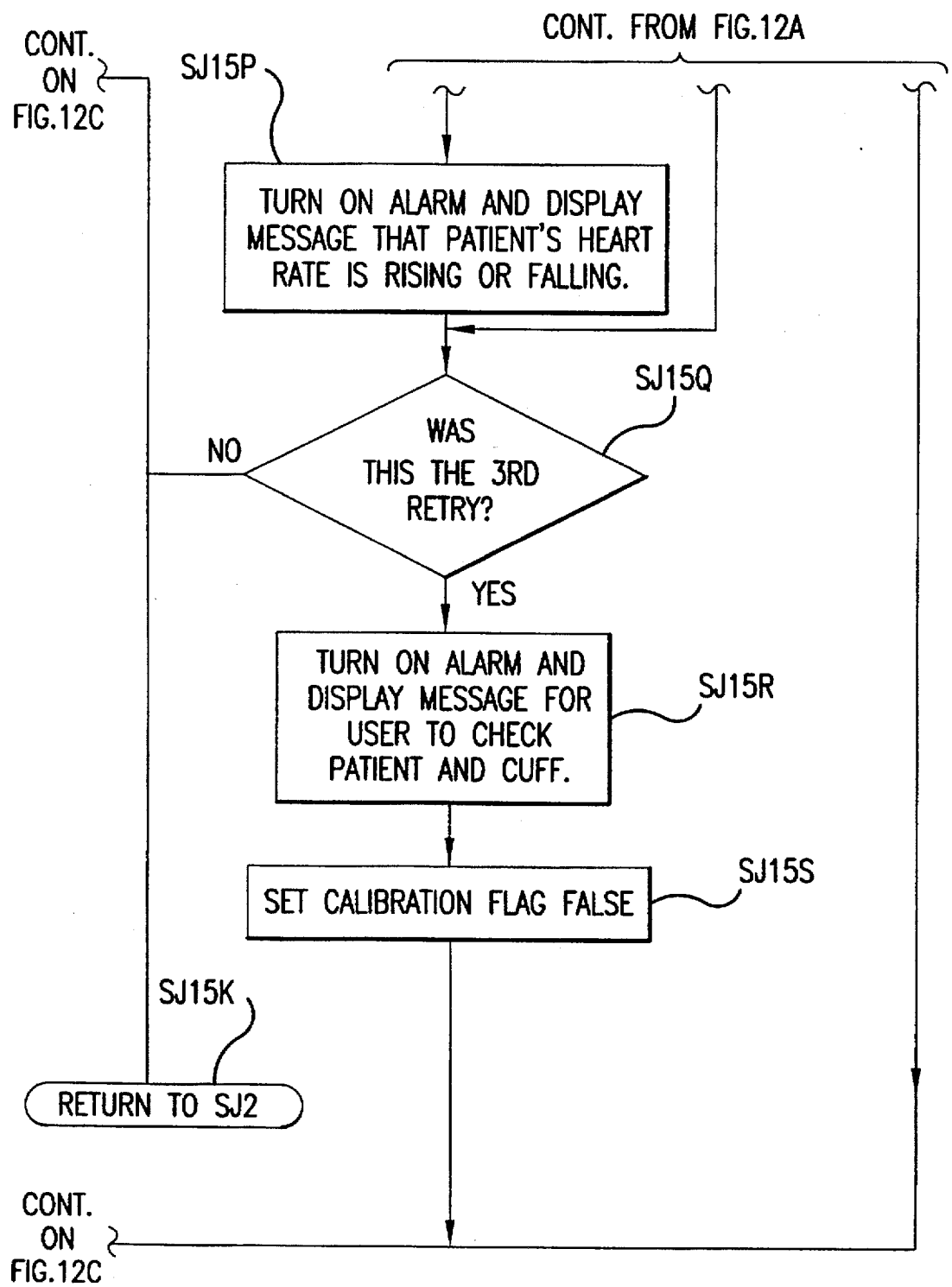
Figure 12C:
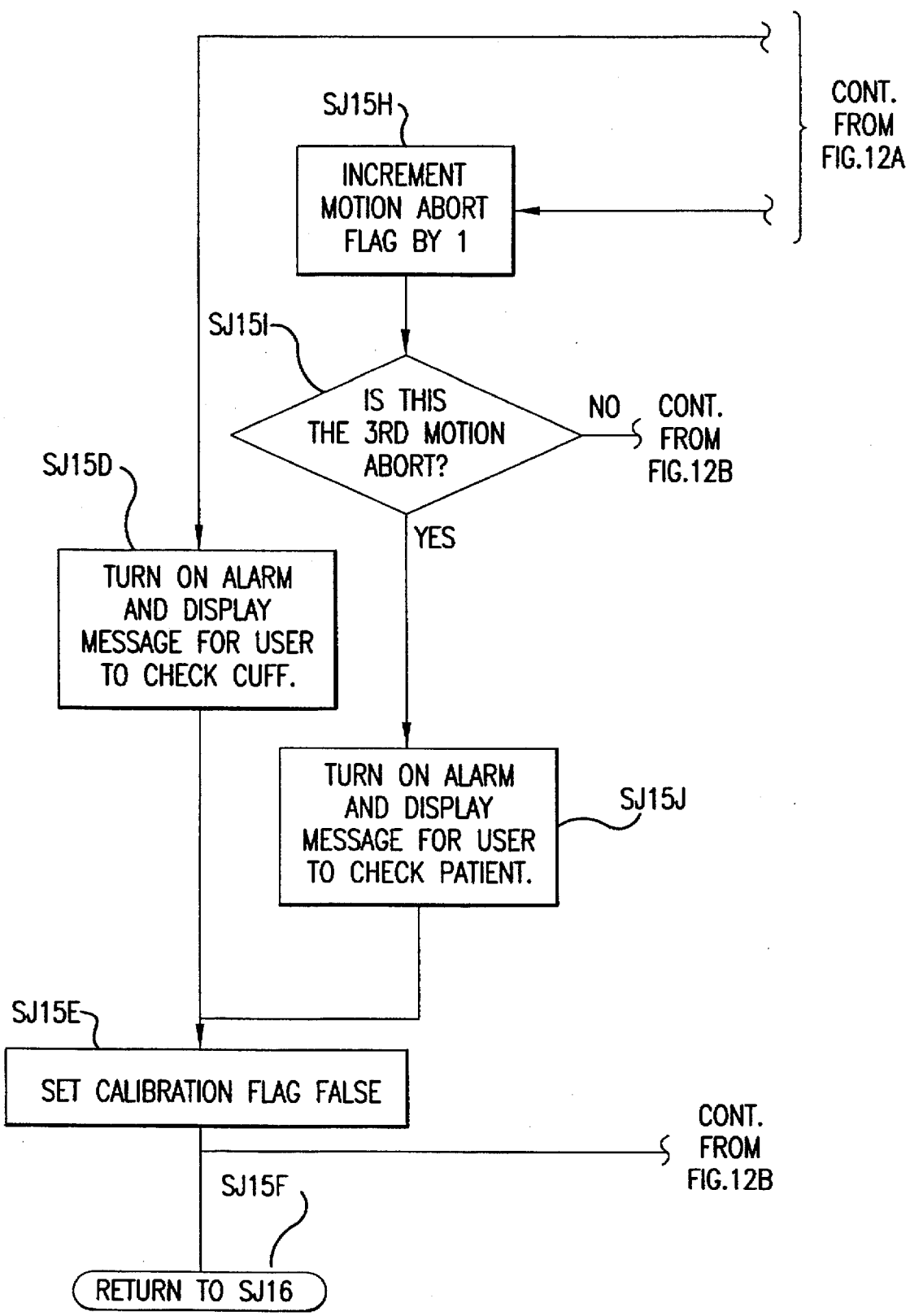

FIGS. 12A–12C show a preferred control routine for the aborted measurement evaluation process of step SJ15. The routine starts at step SJ15A and continues to step SJ15B, where the control routine sets all data quality flags to "FALSE."

Next, at step SJ15C, the control routine determines if the blood-pressure measurement process aborted because the cuff deflation rate was excessively high. An excessively high deflation rate may be caused by leaks in the inflatable cuff 12, the piping 16, or the pressure control system. If the control system determines that the cuff deflation rate was too high, control continues to step SJ15D. Otherwise, control jumps to step SJ15G.

At step SJ15D, the control system turns on an alarm and displays a message on the display device 44 that advises the user to check the cuff system for leaks or other problems. Control then continues to step SJ15E, where the control system sets a Calibration Flag to "FALSE." Next, at step SJ15F, the control system returns to step SJ16.

At step SJ15G, the control system determines if the blood-pressure measurement process was aborted due to motion artifacts. Motion artifacts can occur due to excessive motion by the living subject. If the blood-pressure measurement process aborted due to motion artifacts, control continues to step SJ15H. Otherwise, control jumps to step SJ15L.

At step SJ15H, the control system increments a Motion Abort flag by one. Control then continues to step SJ15I, where the control system determines the value of the Motion Abort flag. If the Motion Abort flag is equal to "3," indicating a third motion abort, control continues to step SJ15J. Otherwise, control jumps to step SJ15K, where the control system returns to step SJ2.

At step SJ15J, the control system turns on an alarm and displays a message on the display device 44 notifying the user to check the patient. Control then jumps to step SJ15E.

At step SJ15L, the control system determines if the blood-pressure measurement process was aborted due to a low pulse amplitude. Low oscillometric pulse amplitudes can be caused by instrument conditions, e.g., an excessively loose cuff 12 or obstructions in the air flow system. Low oscillometric pulse amplitudes can also be caused by physiologic conditions such as low blood pressure due to shock. If the low oscillometric pulse amplitude is caused by a physiologic condition, it is important for the user to know if the low-pulse-amplitude condition is due to a low heart rate or if the cardiovascular system is attempting to compensate by increasing the heart rate.

If the blood-pressure measurement process aborted due to a low oscillometric pulse amplitude, control continues to step SJ15M. Otherwise, control jumps to step SJ15F, where the control system returns to step SJ16.

At step SJ15M, the control system determines if the estimated blood pressure obtained from the estimated-blood-pressure determining circuit 96 is falling. If the control system determines that the estimated blood pressure is falling, control continues to step SJ15N. Otherwise, control jumps to step SJ15O.

At step SJ15N, the control system turns on an alarm and displays a message on the display device 44 notifying the user that the subject's blood pressure may be falling. Next, at step SJ15O, the control system determines if the subject's heart rate is increasing or decreasing. If the subject's heart rate is increasing or decreasing, control continues to step SJ15P. Otherwise, control jumps to step SJ15Q.

At step SJ15P, the control system turns on an alarm and displays a message on the display device 44 notifying the user that the subject's heart rate is rising or falling.

At step SJ15Q, the control system determines if the current attempt to measure the subject's blood pressure was the third attempt. If so, control continues to step SJ15R. Otherwise, control jumps to step SJ15K.

At step SJ15R, the control system turns on an alarm and displays a message on display device 44 notifying the user that the subject and the inflatable cuff 12 should be checked. Control then continues to step SJ15S, where the control system sets a Calibration Flag to "FALSE." Control then jumps to step SJ15F, where the control system returns to step SJ16.

Figure 13A:
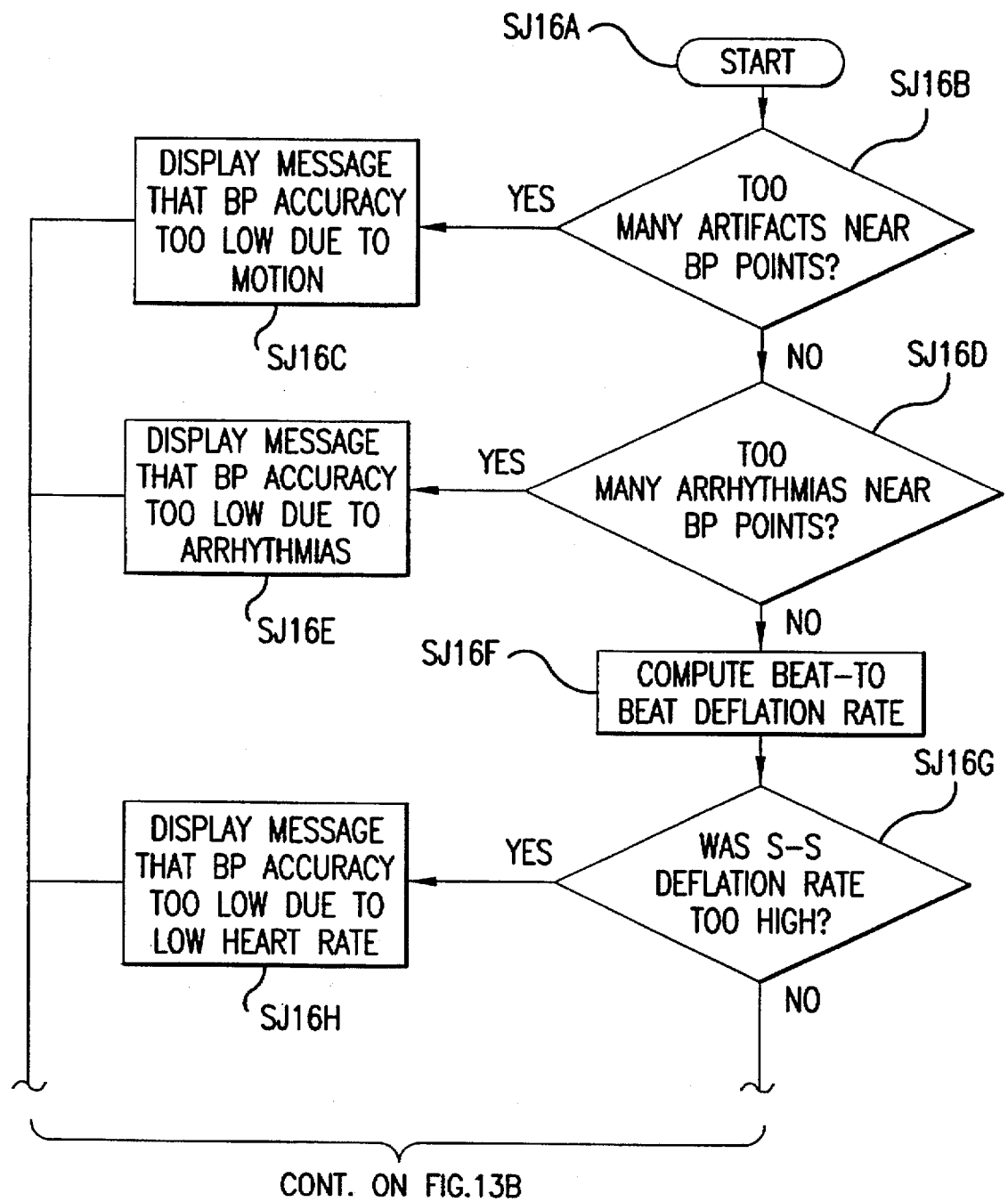
FIGS. 13A to 13C show a flowchart of a preferred control subroutine for evaluating an accuracy of an oscillometric blood-pressure measurement.
Figure 13B:
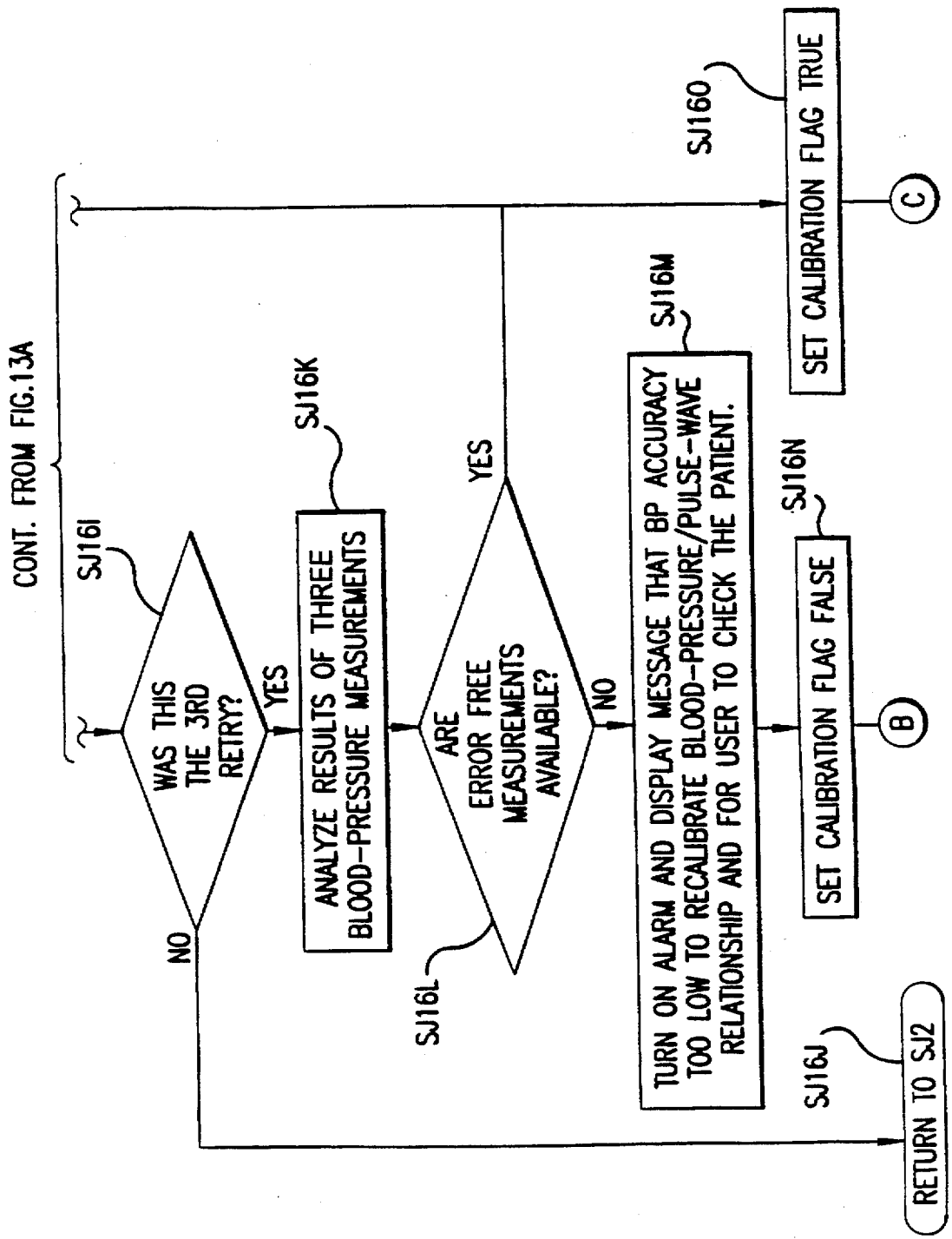
Figure 13C:
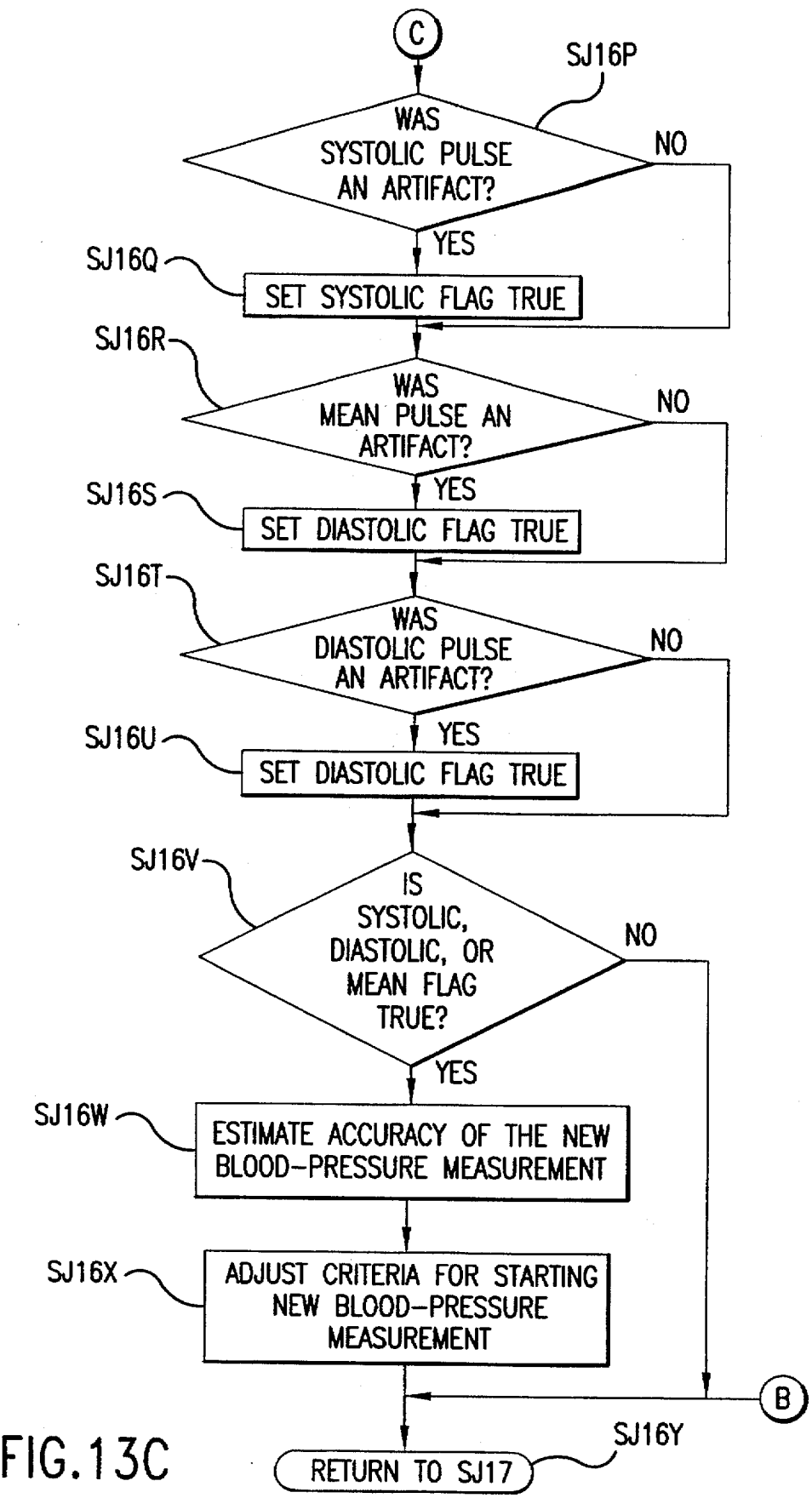

A preferred control routine for evaluating the accuracy of the oscillometric blood-pressure measurement (step SJ16) is shown in FIGS. 13A to 13C. The routine starts at step SJ16A and proceeds to step SJ16B, where the control system determines whether any of the oscillometric pulses before and after the pulses used to determine the systolic blood pressure, diastolic blood pressure and mean blood pressure are artifacts. In addition, the control system determines how many actual pulses were detected during the oscillometric blood-pressure measurement as a percentage of the total number of heartbeats during the oscillometric blood-pressure measurement. The control system assesses the effect of the artifacts on the determined blood pressures using predetermined criteria, e.g., the number of sequential artifacts and the magnitude of the cuff pressure change between the oscillometric pulses used in the determination of the blood pressures. If the control system determines that the errors produced by the artifacts are too high, control continues to step SJ16C. Otherwise, control jumps to step SJ16D.

At step SJ16C, the control system displays a message on display device 44 notifying the user that the blood-pressure accuracy is too low due to motion artifacts, and that the measurement will be repeated. Control then jumps to step SJ16I.

At step SJ16D, the control system measures the number of arrhythmic pulses that occurred before and after the pulses used to determine the systolic blood pressure, diastolic blood pressure and mean blood pressure during the oscillometric blood-pressure measurement. If the number of arrhythmic pulses is greater than a predetermined value, control continues to step SJ16E. Otherwise, control jumps to step SJ16F.

At step SJ16E, the control system sounds an alarm and displays a message on the display device 44, notifying the user that the blood-pressure accuracy is too low due to an excessive number of arrhythmic pulses, and that the measurement will be repeated. Control then jumps to step SJ16I.

At step SJ16F, the control system determines the average change in cuff pressure between heartbeats during the oscillometric blood-pressure measurement. Next, at step SJ16G, the control system determines if the average change in cuff pressure between heartbeats exceeds a predetermined value. If so, control continues to step SJ16H. Otherwise, control jumps to step SJ16O.

At step SJ16H, the control system sounds an alarm and displays a message on display device 44, notifying the user that the blood pressure accuracy is too low due to a low heart rate. Control then continues to step SJ16I.

Next, at step SJ16I, the control system determines if this was the third consecutive time the blood pressure accuracy was too low. If not, control continues to step SJ16J, where the control system returns to step SJ2. Otherwise, control jumps to step SJ16K.

At step SJ16K, the control system analyzes the results of the three blood-pressure measurements. Next, at step SJ16L, the control system determines if error-free systolic blood-pressure value, the error-free diastolic blood-pressure value and the error-free mean blood-pressure value can be obtained from the combination of the three oscillometric blood-pressure measurements. If not, control continues to step SJ16M. If error-free measurements are available, control jumps to step SJ16O.

At step SJ16M, the control system turns on an alarm and displays a message on the display device 44, notifying the user that the accuracy of the blood-pressure measurement is too low to recalibrate the blood-pressure/pulse-wave-velocity relationship, and that the user should check the subject. Next, at step SJ16N, the control system sets the Calibration Flag to "FALSE." Control then jumps to step SJ16Y, where the control system returns to step SJ17.

At step SJ16O, the control system sets the Calibration Flag to "TRUE." Next, at step SJ16P, the control system determines if the pulse at which the systolic blood pressure was measured was an artifact. If so, control continues to step SJ16Q, where the control system sets a Systolic Flag to "TRUE." Otherwise, control jumps to step SJ16R.

At step SJ16R, the control system determines if the pulse at which the mean blood pressure was measured was an artifact. If so, control continues to step SJ16S, where the control system sets a Mean Flag to "TRUE." Otherwise, control jumps to step SJ16T.

At step SJ16T, the control system determines if the pulse at which the diastolic blood pressure was measured was an artifact. If so, control continues to step SJ16U, where the control system sets a Diastolic Flag to "TRUE." Otherwise, control jumps to step SJ16VU.

At step SJ16V, the control system determines if the systolic, diastolic or mean flags are set to "TRUE." If any one of the flags are set to "TRUE", control continues to step SJ16W. Otherwise, control jumps to step SJ16Y.

At step SJ16W, the control system estimates the accuracy of the oscillometric blood-pressure measurements. The control system preferably does this by adding the square of the known error of the oscillometric blood-pressure measurement to the square of the error produced by the increase in the cuff pressure change between heartbeats produced by the deleted artifact. The square root of the sum of the above errors represents the error introduced by the deleted artifact. Next, at step SJ16X, the control system adjusts the criteria used to determine if a new blood-pressure measurement should be made based on the accuracy determined at step SJ16W. Then, at step SJ16Y, the control system returns to step SJ17.

Figure 14:
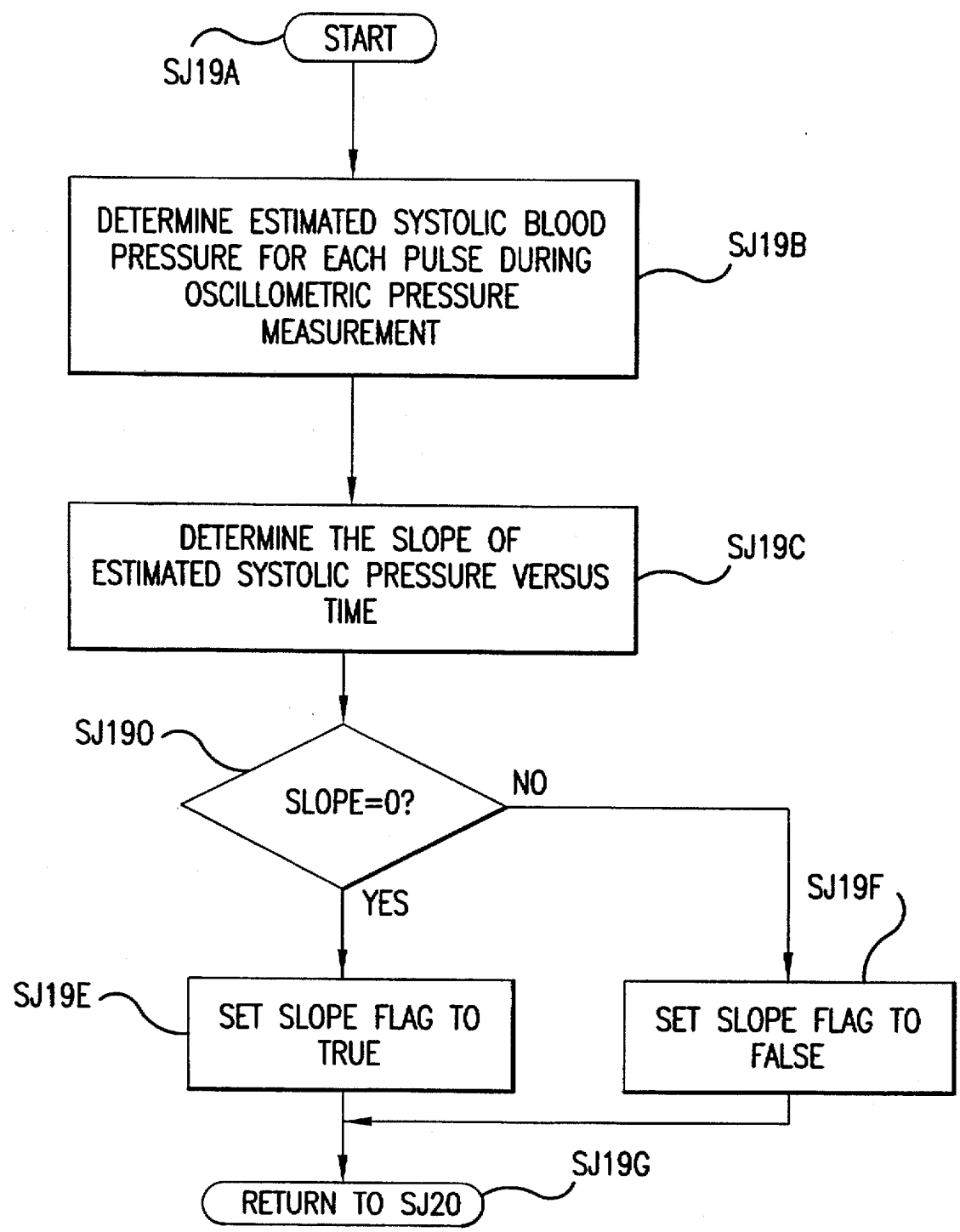
FIG. 14 shows a flowchart of a preferred control subroutine for evaluating changes occuring in a living subject's blood pressure during an oscillometric blood-pressure measurement.

A preferred control routine for evaluating changes in the living subject's blood-pressure during an oscillatory blood-pressure measurement (step SJ19) is shown in FIG. 14. The routine starts at step SJ19A and continues to step SJ19B, where the control system determines the estimated systolic blood pressure for each heartbeat that occurred during the oscillometric blood-pressure measurement using the blood-pressure/pulse-wave-velocity relationship.

Next, at step SJ19C, the control system determines the slope of an estimated blood pressure versus time plot. Next, at step SJ19D, the control system determines if the slope determined as step SJ19C is equal to zero. If the slope is equal to zero, control continues to step SJ19E. Otherwise, control jumps to step SJ19F. At step SJ19E, the control system sets a Slope Flag to "TRUE." Control then jumps to step SJ19G, where the control system returns to step SJ20.

At step SJ19F, the control system sets the Slope Flag to "FALSE." Control then continues to step SJ19G.

A preferred control routine for estimating the systolic blood pressure at the end of the oscillometric blood-pressure measurement (step SJ22) is shown in FIG. 15. The routine starts at step SJ22A and continues to step SJ22B, where the control system obtains, from the blood-pressure measuring circuit 90, the index number of the pulse from which the oscillometric diastolic blood pressure was determined. Next, at step SJ22C, the control system obtains the estimated systolic blood pressure for the pulse from which the diastolic blood pressure was determined. Control then continues to step SJ22D.

At step SJ22D, the control system displays, on the display device 44, the estimated systolic blood pressure and the oscillometric diastolic blood pressure. Next, at step SJ22E, the control system displays an indicator or a message on the display device 44 that notifies the user that the subject's blood pressure was changing during the oscillometric blood-pressure measurement and that the displayed systolic blood pressure is an estimated value. Next, at step SJ22F, the control system returns to step SJ26.

A preferred control routine for performing the user-specified living subject status evaluation checks (step SN) is shown in FIG. 16. The routine starts at step SN1 and proceeds to step SN2, where the control system determines if the user has requested any patient data checks. If the user has requested patient data checks, control continues to step SN3. Otherwise, control jumps to step SN8.

At step SN3, the control system retrieves the user-requested checks one at a time from the question storage area 122 for processing. Each user check is constructed as a logic statement, e.g., "IS NEW SYSTOLIC PRESSURE>PREVIOUS SYSTOLIC PRESSURE."

Next, at step SN4, the control system determines if the user check retrieved at step SN3 is true. If the user check is true, control continues to step SN5. Otherwise, control jumps to step SN7.

At step SN5, the control system constructs a user message, preferably by concatenating the variables with language descriptions of their logic symbol, e.g., "GREATER THAN." Alternatively, the control system can simply display the logic symbol. For example, if the user check "IS NEW SYSTOLIC PRESSURE>PREVIOUS SYSTOLIC PRESSURE" is true, the control system would produce the message "SYSTOLIC PRESSURE IS GREATER THAN PREVIOUS SYSTOLIC PRESSURE," or the more simple message "SYSTOLIC PRESSURE>PREVIOUS SYSTOLIC PRESSURE."

Next, at step SN6, the control system displays the user check message constructed at step SN5. If the user specifies, the control system will also sound an alarm when the message is displayed. Next, at step SN7, the control system determines if all user-entered patient data checks have been completed. If all patient data checks have been completed, control continues to step SN8, where the control system returns to step SO. Otherwise, control returns to step SN3.

The electronic control device 28, including the cuff-pressure regulating circuit 88, the pulse-wave filter circuit 26, the static-pressure filter circuit 24, the blood-pressure measuring circuit 90, the arrhythmia-pulse correcting circuit 114, the oscillometric-systolic-pressure correcting circuit 116, the quality-assurance and data-checking circuit 118, the blood-pressure/pulse-wave-propagation-information relationship determining circuit 94, the estimated blood-pressure determining circuit 96, the estimated-blood-pressure-abnormality judging circuit 108, the pulse-wave-area-abnormality judging circuit 110, the pulse-period-abnormality judging circuit 112, the pulse-wave-propagation-information-obtaining circuit 92, the pulse-wave-area determining circuit 104, the relationship-correcting circuit 102, the heart-rate measuring circuit 100 and the pulse-period measuring circuit 98, is preferably implemented using a programmed general purpose computer. However, the electronic control device 28 can also be implemented using a special purpose computer, a programmed microprocessor or microcontroller and peripheral integrated circuit elements, and ASIC or other integrated circuit, a hard-wired electronic or logic circuit, such as a discrete element circuit, a programmable logic device such as a FPGA, a PLD, a PLA or a PAL, or the like. In general, any device in which a finite state machine capable of implementing the flowcharts shown in FIGS. 8–15 and capable of controlling the peripheral devices shown in FIGS. 2–4 can be used to implement the electronic control device 28 of this invention.

While this invention has been described in conjunction with the specific embodiment outlined above, it is evident that many alternatives, modifications and variations will be apparent to those skilled in the art. For example, in the preferred embodiment, the pulse-wave propagation-information obtaining circuit 92 determines the time difference $DT_{RP}$ between an R point on the electrocardiographic waveform and a minimum point of the living subject's pulse-wave detected by the photoelectric pulse-wave detector 56. However, the time difference may also be calculated from a Q point or an S point of the electrocardiographic waveform to a maximum point or minimum point on the living subject's pulse wave. In general, the time difference may be calculated between any predetermined periodic point on the electrocardiographic waveform and any predetermined periodic point on the living subject's pulse wave.

Accordingly, the preferred embodiments of the invention as set forth above are intended to be illustrative, not limiting. Various changes may be made without departing from the spirit and scope of the invention as defined in the following claims.

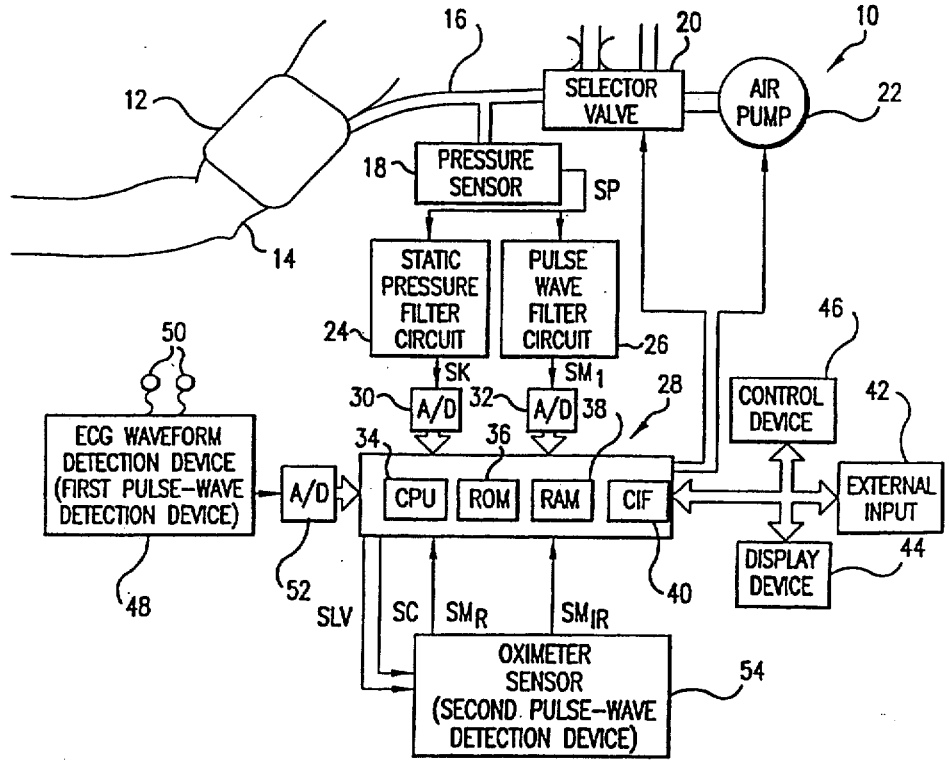

What is claimed is:

1. A system for correcting a living subject's measured blood pressure when the living subject's actual blood pressure changes during an oscillometric blood-pressure measurement, comprising:

an oscillometric pulse-wave detection device that detects oscillometric pressure pulse waves produced by a cardiac muscle of a living subject during the oscillometric-blood-pressure measurement, the oscillometric pressure pulse waves propagating through an artery of the living subject;

a blood-pressure measuring circuit that measures a blood pressure of the living subject based on amplitudes of the oscillometric pressure pulse waves detected by the oscillometric pulse-wave detection device; and an oscillometric-systolic-pressure correcting circuit that corrects a blood pressure measured by the blood-pressure measuring circuit when the living subject's blood pressure changes during the oscillometric-blood-pressure measurement, wherein the oscillometricsystolic-pressure correcting circuit identifies a pulse wave that was used by the blood-pressure measuring circuit to determine a diastolic blood pressure of the living subject.

2. The system of claim 1, wherein the oscillometric-pulse-wave detection device comprises a constriction device that applies a changing constriction pressure to a portion of the living subject.

3. The system of claim 2, wherein the constriction device comprises:
- a cuff wrapable around the portion of the living subject and capable of applying a constriction pressure to the portion of the living subject when the cuff is wrapped around the portion of the living subject; and
- a cuff-pressure regulating circuit that controls the constriction pressure applied by the cuff to the portion of the living subject, the cuff pressure regulating circuit changing the constriction pressure applied by the cuff to the portion of the living subject during an oscillometric-blood-pressure measurement.

4. The system of claim 1, further comprising:
- a first pulse-wave detection device that detects first pulse waves from a first portion of the living subject;
- a second pulse-wave detection device that detects second pulse waves from a second portion of the living subject;
- a pulse-wave-propagation information obtaining circuit that determines time differences between predetermined periodic points on the pulse waves detected by the first pulse-wave detection device and predetermined periodic points on the corresponding pulse waves detected by the second pulse-wave detection device;
- a blood-pressure/pulse-wave-propagation-information relationship determining circuit that determines a relationship between the time differences determined by the pulse-wave-propagation information obtaining circuit and a blood pressure of the living subject; and
- an estimated-blood-pressure determining circuit that successively determines an estimated blood pressure based on the relationship determined by the blood-pressure/pulse-wave-propagation-information relationship determining circuit.

5. The system of claim 4, wherein the first pulse-wave detection device comprises an electrocardiographic waveform detection device.

6. The system of claim 4, wherein the second pulse-wave detection device comprises an oximeter sensor.

7. The system of claim 6, wherein the oximeter sensor comprises a photoelectric pulse-wave detector.

8. The system of claim 4, wherein, when the estimated blood pressure of the living subject changes by a predetermined amount during the oscillometric-blood-pressure measurement, displays an estimated systolic blood pressure for the pulse wave from which the diastolic blood pressure was determined.

9. The system of claim 4, wherein the blood-pressure/pulse-wave-propagation-information relationship determining circuit determines a relationship between the time differences determined by the pulse-wave-propagation information obtaining circuit and a systolic blood pressure of the living subject.

10. The system of claim 4, wherein the pulse-wave-propagation information obtaining circuit further determines pulse wave propagation rates from the determined time differences, and the blood-pressure/pulse-wave-propagation-information relationship determining circuit further determines a relationship between the pulse wave propagation rates determined by the pulse-wave-propagation information obtaining circuit and a blood pressure of the living subject.

11. The system of claim 10, wherein the blood pressure of the living subject is a systolic blood pressure of the living subject.

12. A method of correcting a living subject's measured blood-pressure when the living subject's actual blood-pressure changes during an oscillometric blood-pressure measurement, comprising:
- measuring a blood pressure of a living subject; determining whether the living subject's blood pressure changed during the blood pressure measurement; and
- correcting the measured blood pressure when it is determined that the living subject's blood pressure changed during the blood pressure measurement, wherein, correcting the measured blood pressure comprises identifying a pulse wave used to determine a diastolic blood pressure of the living subject.

13. The method of claim 12, wherein measuring the living subject's blood pressure comprises:
- detecting oscillometric pressure pulse waves from a first portion of the living subject; and
- measuring the living subject's blood pressure based on amplitudes of the oscillometric pressure pulse waves.

14. The method of claim 13, wherein determining whether the living subject's blood pressure changed during the blood pressure measurement comprises:
- detecting first pulse waves from a second portion of the living subject;
- detecting second pulse waves from a third portion of the living subject;
- determining time differences between predetermined periodic points on the first pulse waves detected from the second portion of the living subject and predetermined periodic points on corresponding ones of the second pulse waves detected from the third portion of the living subject;
- determining a relationship between the determined time differences and the living subject's blood pressure;
- determining an estimated blood pressure of the living subject based on the determined relationship;
- determining that the living subject's blood pressure has changed when the estimated blood pressure of the living subject changes by a predetermined amount.

15. The method of claim 14, wherein correcting the measured blood pressure further comprises:
- displaying an estimated systolic blood pressure for the pulse wave from which the diastolic blood pressure was determined.

16. The method of claim 14, wherein detecting first pulse waves from a second portion of the living subject comprises detecting an electrocardiographic waveform from a second portion of the living subject.

17. The method of claim 14, wherein detecting second pulse waves from a third portion of the living subject comprises detecting a plethysmographic pulse wave from a third portion of the living subject.

18. The method of claim 14, wherein determining a relationship between the determined time differences and the living subject's blood pressure comprises determining a relationship between the determined time differences and the living subject's systolic blood pressure.

19. The method of claim 14, wherein determining a relationship between the determined time differences and the living subject's blood pressure comprises:

determining pulse wave propagation rates from the determined time differences;

determining a relationship between the determined pulse wave propagation rates and the living subject's blood pressure.

20. The method of claim 19, wherein determining a relationship between the determined pulse wave propagation rates and the living subject's blood pressure comprises determining a relationship between the determined pulse wave propagation rates and the living subject's systolic blood pressure.

* * * * *

UNITED STATES PATENT AND TRADEMARK OFFICE
CERTIFICATE OF CORRECTION

PATENT NO. :
DATED :  5,895,359
INVENTOR(S) :  April 20, 1999
Harry H. PEEL, III Page 1 of 19

It is certified that error appears in the above-identified patent and that said Letters Patent is hereby corrected as shown below:

Title page, showing the illustrative should be deleted and replaced with the attached Title page.

IN THE DRAWINGS:

Substitute the attached replacement figures, Figs. 1, 2, 5A, 5B, 8, 9B, 12A-C, 13A-C and 14 for the corresponding original figures.

Signed and Sealed this

Thirty-first Day of October, 2000

Attest:

Attesting Officer

Q. TODD DICKINSON

Director of Patents and Trademarks

UNITED STATES PATENT AND TRADEMARK OFFICE
CERTIFICATE OF CORRECTION

PATENT NO. : 5,895,359  
DATED : April 20, 1999  
INVENTOR(S) : Harry H. PEEL, III Page 2 of 19

It is certified that error appears in the above-identified patent and that said Letters Patent is hereby corrected as shown below:

IN THE SPECIFICATION:

| | | |
|---|---|---|
| Col. 4, | line 23, | change "5C" to --5B--. |
| Col. 13, | line 64, | change "$P_c$" to --SP--. |
| Col. 14, | line 7, | change "$P_c$" to --SP--. |
| Col. 17, | line 13, | change "SP"(second occurrence) to --SR--. |
| Col. 20, | line 8, | change "SJ15" to --SJ16--; |
| | line 9, | change "SJ15A" to --SJ16A-- and change "SJ15B" to --SJ16B--. |
| | line 12, | change "SJ15C" to --SJ16C--; |
| | line 18, | change "SJ15D" to --SJ16D--; |
| | line 19, | change "SJ15G" to --SJ16G--; |
| | line 20, | change "SJ15D" to --SJ16D--; |
| | line 23, | change "SJ15E" to --SJ16E--; |
| | line 25, | change "SJ15F" to --SJ16F-- and change "SJ16" to --SJ17--; |
| | line 26, | change "SJ15G" to --SJ16G--; |
| | line 31, | change "SJ15H" to --SJ16H--; |
| | line 32, | change "SJ15L" to --SJ16L--; |
| | line 33, | change "SJ15H" to --SJ16H--; |
| | line 34, | change "SJ15I" to --SJ16I--; |
| | line 37, | change "SJ15J" to --SJ16J--; |
| | line 38, | change "SJ15K" to --SJ16K--; |
| | line 40, | change "SJ15J" to --SJ16J--; |
| | line 42, | change "SJ15E" to --SJ16E--; |
| | line 43, | change "SJ15L" to --SJ16L--; |
| | line 57, | change "SJ15M" to --SJ16M-- and change "SJ15F" to --SJ16F--; |

UNITED STATES PATENT AND TRADEMARK OFFICE
CERTIFICATE OF CORRECTION

Page 3 of 19

PATENT NO. : 5,895,359
DATED : April 20, 1999
INVENTOR(S) : Harry H. PEEL, III

It is certified that error appears in the above-identified patent and that said Letters Patent is hereby corrected as shown below:

|  |  |  |
|---|---|---|
|  | line 58, | change "SJ16" to --SJ17--; |
|  | line 59, | change "SJ15M" to --SJ16M--; |
|  | line 63, | change "SJ15N" to --SJ16N--; |
|  | line 64, | change "SJ15O" to --SJ16O--; |
|  | line 65, | change "SJ15N" to --SJ16N--; |
| Col. 21. | line 1, | change "SJ15O" to --SJ16O--; |
|  | line 4, | change "SJ15P" to --SJ16P-- and change "SJ15Q" to --SJ16Q--; |
|  | line 5, | change "SJ15P" to --SJ16P--; |
|  | line 8, | change "SJ15Q" to --SJ16Q--; |
|  | line 10, | change "SJ15R" to --SJ16R--; |
|  | line 11, | change "SJ15K" to --SJ16K--. |
|  | line 12, | change "SJ15R" to --SJ16R--; |
|  | line 15, | change "SJ15S" to --SJ16S--; |
|  | line 17, | change "SJ15F" to --SJ16F--; |
|  | line 18, | change "SJ16" to --SJ17--; |
|  | line 20, | change "SJ16" to --SJ17--; |
|  | line 21, | change "SJ16A" to --SJ17A--; |
|  | line 22, | change "SJ16B" to --SJ17B--; |
|  | line 37, | change "SJ16C" to --SJ17C--; |
|  | line 38, | change "SJ16D" to --SJ17D--; |
|  | line 39, | change "SJ16C" to --SJ17C--; |
|  | line 43, | change "SJ16I" to --SJ17I--; |
|  | line 44, | change "SJ16D" to --SJ17D--; |
|  | line 50, | change "SJ16E" to --SJ17E--; |
|  | line 51, | change "SJ16F" to --SJ17F--; |

UNITED STATES PATENT AND TRADEMARK OFFICE
CERTIFICATE OF CORRECTION

Page 4 of 19

PATENT NO. : 5,895,359
DATED : April 20, 1999
INVENTOR(S) : Harry H. PEEL, III

It is certified that error appears in the above-identified patent and that said Letters Patent is hereby corrected as shown below:

|  |  |  |
|---|---|---|
| | line 52, | change "SJ16E" to --SJ17E--; |
| | line 56, | change "SJ16I" to --SJ17I--; |
| | line 57, | change "SJ16F" to --SJ17F--; |
| | line 59, | change "SJ16G" to --SJ17G--; |
| | line 62, | change "SJ16H" to --SJ17H--; |
| | line 63, | change "SJ16O" to --SJ17O--; |
| | line 64, | change "SJ16H" to --SJ17H--; |
| | line 67, | change "SJ16I" to --SJ17I--; |
| Col. 22, | line 1, | change "SJ16I" to --SJ17I--; |
| | line 3, | change "SJ16J" to --SJ17J--; |
| | line 5, | change "SJ16K" to --SJ17K--; |
| | line 6, | change "SJ16K" to --SJ17K--; |
| | line 7, | change "SJ16L" to --SJ17L--. |
| | line 13, | change "SJ16M" to --SJ17M--; |
| | line 14, | change "SJ16O" to --SJ17O--; |
| | line 15, | change "SJ16M" to --SJ17M--; |
| | line 20, | change "SJ16N" to --SJ17N--; |
| | line 22, | change "SJ16Y" to --SJ17Y-- and change "SJ17" to --SJ18--; |
| | line 23, | change "SJ16O" to --SJ17O--; |
| | line 24, | change "SJ16P" to --SJ17P--; |
| | line 27, | change "SJ16Q" to --SJ17Q--; |
| | line 28, | change "SJ16R" to --SJ17R--; |
| | line 29, | change "SJ16R" to --SJ17R--; |
| | line 31, | change "SJ16S" to --SJ17S--; |
| | line 33, | change "SJ16T" to --SJ17T--; |

UNITED STATES PATENT AND TRADEMARK OFFICE
CERTIFICATE OF CORRECTION

Page 5 of 19

PATENT NO. : 5,895,359
DATED : April 20, 1999
INVENTOR(S) : Harry H. PEEL, III

It is certified that error appears in the above-identified patent and that said Letters Patent is hereby corrected as shown below:

|          |          |                                                                              |
|----------|----------|------------------------------------------------------------------------------|
|          | line 34, | change "SJ16T" to --SJ17T--;                                                 |
|          | line 36, | change "SJ16U" to --SJ17U--;                                                 |
|          | line 38, | change "SJ16VU" to --SJ17V--;                                                |
|          | line 39, | change "SJ16V" to --SJ17V--;                                                 |
|          | line 42, | change "SJ16W" to --SJ17W-- and change "SJ16Y" to --SJ17Y--;                  |
|          | line 43, | change "SJ16W" to --SJ17W--;                                                 |
|          | line 51, | change "SJ16X" to --SJ17X--;                                                 |
|          | line 54, | change "SJ16W" to --SJ17W-- and change "SJ16Y" to --SJ17Y--;                  |
|          | line 55, | change "SJ17" to --SJ18--;                                                   |
|          | line 58, | change "SJ19" to --SJ20--;                                                   |
|          | line 59, | change "SJ19A" to --SJ20A-- and change "SJ19B" to --SJ20B--;                  |
|          | line 64, | change "SJ19C" to --SJ20C--;                                                 |
|          | line 66, | change "SJ19D" to --SJ20D--;                                                 |
|          | line 67, | change "SJ19C" to --SJ20C--;                                                 |
| Col. 23, | line 1,  | change "SJ19E" to --SJ20E--;                                                 |
|          | line 2,  | change "SJ19F" to --SJ20F-- and change "SJ19E" to --SJ20E--;                  |
|          | line 4,  | change "SJ19G" to --SJ20G-- and change "SJ20" to --SJ21--;                    |
|          | line 5,  | change "SJ19F" to --SJ20F--;                                                 |
|          | line 6,  | change "SJ19G" to --SJ20G--.                                                 |

United States Patent [19]
Peel, III

[11] Patent Number: 5,895,359
[45] Date of Patent: Apr. 20, 1999

[54] SYSTEM AND METHOD FOR CORRECTING A LIVING SUBJECT'S MEASURED BLOOD PRESSURE

[75] Inventor: Harry H. Peel, III, San Antonio, Tex.

[73] Assignee: Southwest Research Institute, San Antonio, Tex.

[21] Appl. No.: 08/870,456

[22] Filed: Jun. 6, 1997

[51] Int. Cl.$^6$ .................................................. A61B 5/00
[52] U.S. Cl. ...................................................... 600/494
[58] Field of Search .............................. 600/490, 491, 600/492, 493, 494, 495, 496, 500

[56] References Cited

U.S. PATENT DOCUMENTS 5,131,391 7/1992 Sakai et al. .
5,752,920 5/1998 Ogura et al. ........................ 600/494

FOREIGN PATENT DOCUMENTS 0 123 313 10/1984 European Pat. Off. .
0 815 790 A1 1/1998 European Pat. Off. .
0 821 910 A2 2/1998 European Pat. Off. .

Primary Examiner—Scott M. Getzow
Attorney, Agent, or Firm—Oliff & Berridge, PLC

[57] ABSTRACT

A system and method for correcting a living subject's measured blood pressure when the living subject's actual blood pressure changes during an oscillometric blood pressure measurement detects oscillometric pressure pulse waves produced by a cardiac muscle of the living subject, measures a blood pressure of the living subject based on the amplitudes of the oscillometric pressure pulse waves, and corrects the measured blood pressure when the living subject's blood pressure changes during the blood pressure measurement. The system and method of this invention preferably determine an estimated blood pressure of the living subject, monitor the estimated blood pressure, and determine that the living subject's blood pressure changed during the blood pressure measurement when the estimated blood pressure changes by a predetermined amount during the blood pressure measurement. When the living subject's blood pressure is determined to have changed during the blood pressure measurement, the system and method of this invention display an estimated systolic blood pressure for the time at which the living subject's diastolic blood pressure was measured.

20 Claims, 23 Drawing Sheets